United States Patent [19]

Muchowski et al.

[11] Patent Number: 4,826,869
[45] Date of Patent: May 2, 1989

[54] N-(LOWER ALKYL)-2-(3'UREIDOBENZYL)PYRROLIDINES

[75] Inventors: Joseph M. Muchowski, Sunnyvale; Robin D. Clark, Palo Alto; L. David Waterbury, San Mateo, all of Calif.

[73] Assignee: Syntex (U.S.A.) Inc., Palo Alto, Calif.

[21] Appl. No.: 158,197

[22] Filed: Feb. 19, 1988

[51] Int. Cl.$^4$ .................... A61K 31/40; C07D 207/09
[52] U.S. Cl. ...................................... 514/408; 548/400
[58] Field of Search ........................ 548/400; 514/408

[56] References Cited

U.S. PATENT DOCUMENTS

| 4,279,918 | 7/1981 | Eistetter et al. | 424/274 |
|---|---|---|---|
| 4,342,692 | 8/1982 | Suh et al. | 260/326.46 |
| 4,426,386 | 1/1984 | Arvidsson et al. | 424/267 |
| 4,454,151 | 6/1984 | Waterbury | 424/245 |
| 4,558,066 | 12/1985 | Waterbury | 514/422 |
| 4,629,730 | 12/1986 | Clark et al. | 514/331 |
| 4,642,378 | 2/1987 | Clark et al. | 564/51 |

FOREIGN PATENT DOCUMENTS 2054581A 2/1981 United Kingdom .

Primary Examiner—Joseph Paul Brust
Attorney, Agent, or Firm—David A. Lowin; Tom M. Moran

[57] ABSTRACT

N-(lower alkyl)-2-(3'-ureidobenzyl)pyrrolidines and N-(lower alkyl)-2-(3'-ureidobenzyl)-5-(lower alkyl)pyrrolidines are useful for lowering intraocular pressure in mammals, for example, in the treatment of glaucoma.

22 Claims, No Drawings

N-(LOWER ALKYL)-2-(3'UREIDOBENZYL)PYRROLIDINES

BACKGROUND OF THE INVENTION

1. Field of the Invention

The present invention relates to pharmaceutical compositions, particularly to a series of N-(lower alkyl)-2-(3'-ureidobenzyl)pyrrolidines, methods of synthesizing the same, and to their use as agents for lowering intra ocular pressure ("IOP"), for example, in the treatment of glaucoma.

2. Background Information

A variety of compounds have been described for use in lowering IOP, including, the dialkyl- or cycloalkylaminoethylaniline derivatives described in U.S. Pat. No. 4,629,730, the aryalkyl-aminoethylanine derivatives described in U.S. Pat. No. 4,642,378, 11-α-methyl emprostil as described in commonly owned, pending U.S. Applications Ser. No. 018,776, filed Feb. 27, 1987, now abandoned and U.S. Application Ser. No. 039,560, filed Apr. 16, 1987, and the widely publicized use of marijuana for treating glaucoma. None of these prior compounds, however, are structurally related to the compounds of the present invention.

U.S. Pat. No. 4,279,918 to Eistetter describes N-(lower alkyl)-2-(3'-substituted benzyl)pyrrolidines, but not the 3'-ureidobenzyl compounds of the present invention and not for use in lowering IOP.

SUMMARY OF THE INVENTION

One aspect of the present invention concerns N-(lower alkyl)-2-(3'-ureidobenzyl)pyrrolidine and 5-(lower alkyl) derivatives thereof, i.e., the compounds of Formula I:

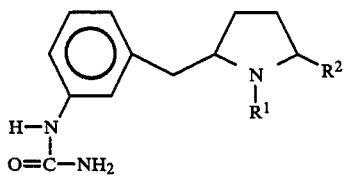

Formula I wherein:

$R^1$ is lower alkyl; and $R^2$ is lower alkyl or hydrogen; and the pharmaceutically acceptable salts thereof, including any single isomer or mixture of isomers thereof.

In another aspect, the invention relates to a pharmaceutical composition containing a therpeutically effective amount of a compound of Formula I or a pharmaceutically acceptable salt thereof admixed with at least one pharmaceutically acceptable excipient.

In yet another aspect, the invention relates to a method of reducing intraocular pressure in a mammal, for example in the treatment of glaucoma, by administering to a mammal in need thereof a therapeutically effective amount of a compound of Formula I or a pharmaceutically acceptable salt thereof.

DETAILED DESCRIPTION OF THE INVENTION

Definitions and General Parameters

The following definitions are set forth to illustrate and define the meaning and scope of the various terms used to describe the invention herein.

The compounds of Formula I are named and numbered as described below. With respect to the nomenclature employed in naming the compounds of the invention, for example, the compound of Formula I where $R^1$ is propyl and $R^2$ is hydrogen, i.e., the compound of Formula II:

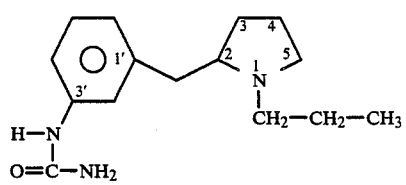

Formula II is named 1-n-propyl-2-(3'-ureidobenzyl)pyrrolidine.

The compound where $R^1$ is propyl and $R^2$ is propyl, i.e., the compound of Formula III:

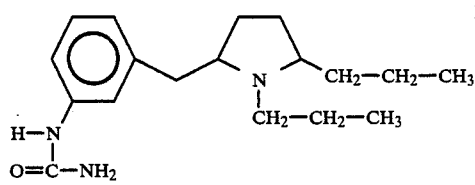

Formula III in named 1,5-di-n-propyl-2-(3'-ureidobenzyl)pyrrolidine.

The compound where $R^1$ is propyl and $R^2$ is methyl, i.e., the compound of Formula IV:

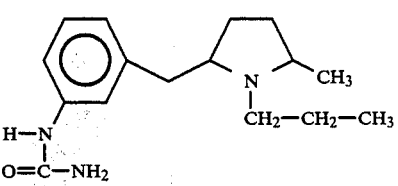

Formula IV is named 1-n-propyl-2-(3'-ureidobenzyl)-5-methylpyrrolidine.

There are two asymmetric centers in the molecules of the present invention, giving rise to isomers. Where $R^2$ is hydrogen, there is one chiral center at the #2 atom of the pyrrolidine and, for purposes of the present invention, no distinction will be made between the possible d- and l-optical isomers. Where $R^2$ is lower alkyl, there are two chiral centers, at the #2 and #5 positions of the pyrrolidine, and the compounds are named as illustrated with respect to Formulae Va, Vb, Vc and Vd.

The isomers of Formulae Va and Vb are the "cis" form, i.e., the substituents at the 2 position and at the 5 position are both above or below the plane. For example, the compound where $R^1$ is propyl and $R^2$ is propyl is named cis-1,5-di-n-propyl-2-(3'-ureidobenzyl)pyrrolidine.

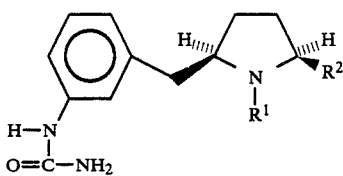

Formula Va

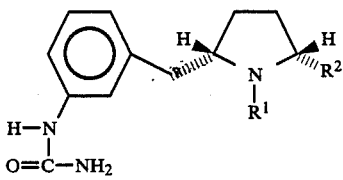

Formula Vb

The isomers of Formulae Vc and Vd are the "trans" form, i.e., one of the substituents at the 2 position or the 5 position is above and the other is below the plane. For example, the compound where $R^1$ is propyl and $R^2$ is propyl is named trans-1,5-di-n-propyl-2-(3′-uriedobenzyl)pyrrolidine.

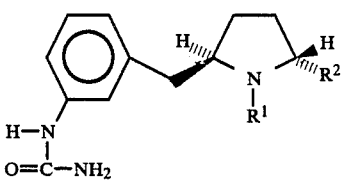

Formula Vc

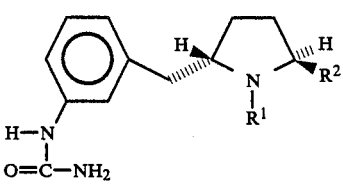

Formula Vd

"Racemic mixture" means a mixture containing equal parts of individual enantiomers. "Non-racemic mixture" is a mixture containing unequal parts of individual enantiomers.

The term "mixture" as applied to Formula I is defined in the present application as any combination of the two components when $R^2$ is hydrogen, and when $R^2$ is lower allkyl, as any combination of the four components (of Formula Va, Vb, Vc and Vd) in any proportions, and all permutations of any two or three of the four components in any proportions.

Isolation, purification and resolution of the compounds and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples hereinbelow. However, other equivalent separation or isolation procedures can, of course, also be used.

As used herein, the term "alkyl" refers to a fully saturated monovalent radical containing only carbon and hydrogen, and which may be a branched or straight chain radical. This term is further exemplified by radicals such as methyl, ethyl, i-butyl, pentyl, pivalyl, heptyl and adamantyl.

The term "lower alkyl" refers to a fully saturated monovalent radical containing only carbon and hydrogen, which may be a branched or straight chain radical of one to six carbon atoms. This term is further exemplified by such radicals as methyl, ethyl, n-propyl, isopropyl, n-butyl, i-butyl (or 2-methylpropyl), i-amyl, n-pentyl, and n-hexyl.

For purposes of the present specification, the n-(lower alkyl) or straight chain form is intended absent some specific indication to the contrary. For example, "2-propylpyrrole" means "2-(n-propyl)pyrrole".

As used herein, the term "halo" refers to fluoro, bromo, chloro and iodo.

The term "acyl" means a radical based on an organic acid, e.g., —C(O)R, where R is alkyl (such as methyl, ethyl . . . ), cycloalkyl (such as cyclohexyl), aryl (such as phenyl) or heterocyclic (such as morpholino).

A "pharmaceutically acceptable salt" may be any salt derived from an inorganic or organic acid. The term "pharmaceutically acceptable anion" refers to the anion of such acid addition salts. The salt and/or the anion are chosen not to be biologically or otherwise undesirable.

The anions are derived from inorganic acids, such as hydrochloric acid, hydrobromic acid, sulfuric acid (giving the sulfate and bisulfate salts), nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, salicyclic acid, p-toluensulfonic acid and the like.

As used herein, the terms "inert organic solvent" or "inert solvent" mean a solvent inert under the conditions of the reaction being described in conjunction therewith [including, for example, benzene, toluene, acetonitrile, tetrahydrofuran ("THF"), diethyl ether, chloroform, methanol, methylene chloride, dimethylformamide ("DMF"), pyridine and the like).

As used herein, the term "treatment" or "treating" means any treatment of a disease in a mammal, including:

(i) preventing the disease, that is, causing the clinical symptoms of the disease not to develop;

(ii) inhibiting the disease, that is, arresting the development of clinical symptoms; and/or (iii) relieving the disease, that is, causing the regression of clinical symptoms.

As used herein, the term "q.s." means adding a quantity sufficient to achieve a stated function, e.g., to bring a solution to the desired volume (i.e., 100%).

Unless specified to the contrary, the reactions described herein take place at atmospheric pressure over a temperature range from about 10° C. to about 100° C., more preferably from about 10° C. to about 50° C., and most preferably at about room (or "ambient") temperature, e.g., about 20° C.

Synthesis of the Compounds of Formula I

The starting material for synthesis of the compounds of the present invention can be unsubstituted pyrrole, 1-(lower alkyl substituted)pyrrole, 2-(lower alkyl substituted)pyrrole, or 1,2-di-(lower alkyl substituted)pyrrole. Unsubstituted pyrrole is available from Aldrich. Substituted pyrroles can be prepared as described herein (see Reaction Schemes 1 and 2) or by other methods known in the art. The compounds of Formula I are all ultimately prepared, as illustrated in Reaction Scheme 3, from a 1-(lower alkyl substituted)-2-(3'-nitrobenzoyl)-5-(optionally lower alkyl substituted)pyrrole.

As used in the Reaction Schemes, the substituents $R^1$ and $R^2$ are the same as in the Summary of the Invention. As described below, the pyrrole portion of the Formula I may be substituted at $R^1$ and/or $R^2$, either in the starting material, or during the course of the synthesis.

Preparation of 2-(lower alkyl substituted)pyrroles

Referring to Reaction Scheme 1, the 2-(lower alkyl substituted)pyrrole starting materials are prepared, for example, by a Vilsmeier-Haack acylation, i.e., the reaction of the complex formed by the reaction of a

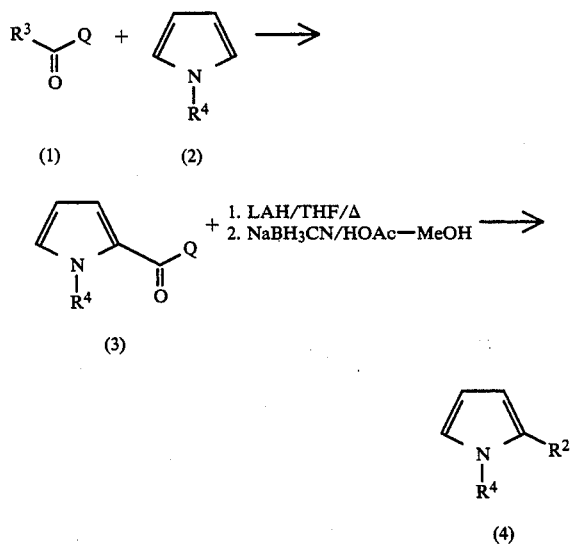

compound of Formula 1, where $R^3$ is hydrogen or lower alkyl and Q is the residue (i.e., all but the N-bonded hydrogen atom) of a dialkylamine [e.g., dimethylamine, ethyl(methyl)amine, and the like] or a saturated cyclic amine (e.g., pyrrolidine, piperidine, morpholine, and the like) and an acid halide (e.g., phosphorus oxychloride, phosphoryl bromide, thiophosphoryl chloride, thionyl chloride, thionyl bromide, phosgene, thiophosgene, oxalyl chloride, thiooxalyl chloride, and the like) with a pyrrole of Formula 2, where $R^4$ can be hydrogen or lower alkyl. Preferred compounds of Formula 1 are the lower alkyl morpholides, and a preferred acid halide is phosphophoryl chloride. These reactions are described in U.S. Pat. Nos. 4,353,829 (morpholides); and 4,089,969 and 4,347,186 (dialkylamides).

Preparation of Formula 3

The compound of Formula 1 is cooled, for example to about $-20°$ to $10°$ C., preferably about $0°$ C., and about one molar equivalent of acid halide (preferably phosphorus oxychloride) is added slowly with stirring. The temperature is allowed to rise slowly to about $20°$ C. to $40°$ C., preferably about $35°$ C., and the mixture is maintained at that temperature for about 8 to 48 hours, preferably about 18 hours.

The mixture is then optionally cooled, for example to about $-20°$ to $10°$ C., preferably about $0°$ C., and about one molar equivalent of pyrrole (1), dissolved in an inert organic solvent (preferably anhydrous 1,2-dichloroethane) is added slowly with stirring. The temperature is allowed to rise slowly to about $10°$ to $40°$ C., preferably about ambient temperature, and the mixture is stirred at that temperature for about 12 to 48 hours, preferably about 24 hours.

The mixture is them poured into an excess of a hydrolysing agent (e.g., a saturated sodium carbonate solution) and heated, preferably to the refluxing temperature of the solvent used, for about 0.5 to 4 hours, preferably about 1.5 hours. After cooling, the solid material is separated by filtration, washed with a large volume of methylene chloride, and separated into two phases.

The organic phase is dried, evaporated in vacuo, and then purified in the usual manner (e.g., by column chromatography over silica gel) to obtain the 2-(lower acyl substituted)pyrrole of Formula 3.

Preparation of Formula 4

A 2-(lower alkyl substituted)pyrrole (3), dissolved in an inert organic solvent (preferably anhydroux THF) is added slowly to a stirred suspension of about one molar equivalent of a reducing agent [such as a hydride of aluminum or boron; preferably lithium aluminum hydride ("LAH")] in the same or a similar solvent. The reaction mixture is heated, preferably to the reflux temperature of the solvent being used, for a period of about 5 minutes to 2 hours, preferably 10 minutes to ;b 1 hour, and most preferably about 30 minutes. The reaction mixture is then cooled (to about $0°$ C.) and the excess reducing agent is destroyed by carefully adding a combination of ethyl acetate, saturated sodium sulfate solution and solid anhydrous sodium sulfate. The insoluble material is removed by filtration and the filtrate evapoated in vacuo to produce a lower alkyl 2-pyrrolyl carbinol (not shown), an unstable intermediate, that is sued without further purification by dissolving it in an inert organic solvent (such as a lower alkanol, preferably methanol), cooling to about $-40°$ to $-20°$ C., preferably $-10°$ C., and treating with a molar excess of reducing agent (sodium cyanoborohydride in glacial acetic acid). The reaction mixture is allowed to warm to about ambient temperature and is stirred for a period of about 0.5 to 3 hours, preferably 1 to 2 hours. The reaction is then quenched (for example, with saturated sodium carbonate) and extracted with ethyl acetate. The extract is washed with water, dried and evaporated in vacuo, and then purified, e.g., by column chromatography over silica gel, to obtain the 2-(lower alkyl substituted)pyrrole of Formula 4.

Optionally, the amount of LAH used can be increased to about 3.5 molar equivalents, the reflux time increased to about 20 to 30 hours, preferably 24 hours, and the desired compound of Formula 4 can be obtained by filtration and standard purification after the excess LAH has been destroyed and the reaction has been quenched.

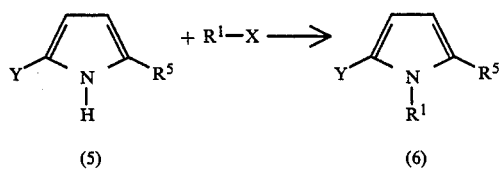

Preparation of N-(lower alkyl substituted)pyrroles

The compounds of Formula I are prepared from a N-(lower alkyl substituted)-2-(3'-nitrobenzoyl)-5-(optionally lower alkyl substituted)pyrrole, which is prepared by N-alkylation of a 2-(optionally lower alkyl or lower acyl substituted)pyrrole either before or after attachment of the 3'-nitrobenzoyl group.

As illustrated in Reaction Scheme 2, about two to three molar equivalents of a metal hydride (preferably sodium hydride) are suspended in an inert organic solvent (preferably anhydrous DMF), preferably under an inert atmosphere. A pyrrole of Formula 5 (in which Y represents hydrogen or a 3'-nitrobenzoyl group, and $R^5$ represents hydrogen, lower alkyl or lower acyl) dissolved in an inert organic solvent (preferably anhydrous DMF) is added slowly thereto. The mixture is stirred at about 23° to 35° C., preferably about ambient temperature, for a period of about 15 minutes to 13 hours, preferably about 2 hours (then optionally cooled to about $-20°$ to 10° C., preferably about 0° C.) followed by the addition of about one to three molar equivalents of a lower alkyl halide ["$R^1-X$,", where X is halo and $R^1$ is the desired lower alkyl group (such as methyl iodide, ethyl iodide, 1-bromopropane, 1-bromobutane, or 2-bromobutane)]. The reaction mixture is stirred for an additional period of about 15 minutes to 48 hours, preferably about 20 hours, and then poured into ethyl acetate, dried and evaporated to give an N-(alkyl substituted)pyrrole of Formula 6.

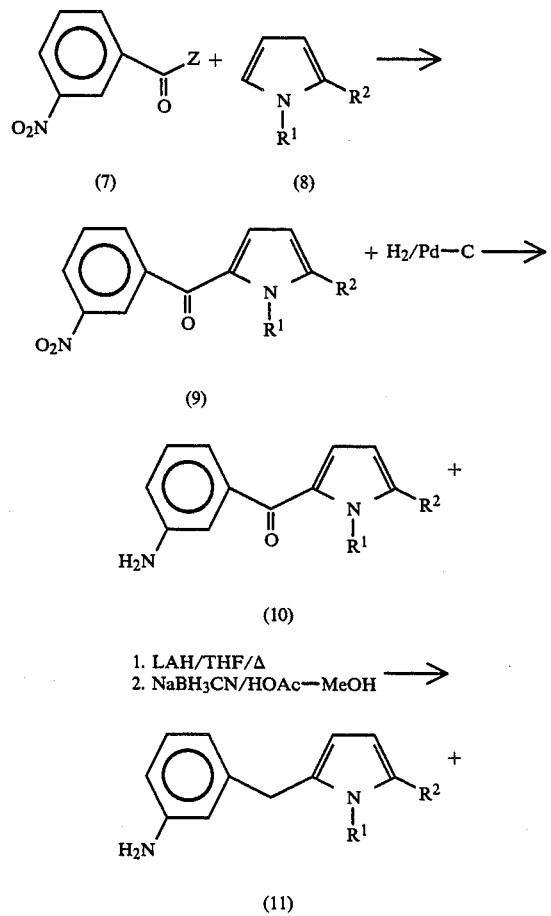

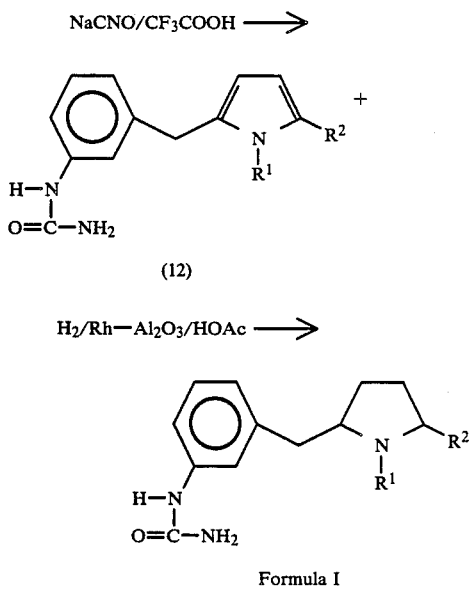

Formula I

Preparation of Intermediate (9)

The compounds of Formula I are prepared, for example, as illustrated in Reaction Scheme 3, by a Vilsmeier-Haack reaction of a m-nitrobenzoylamide or condensation of a m-nitrobenzoyl halide, preferably m-nitrobenzoyl chloride (as represented by Formula 7 wherein Z is Q of halo) with a substituted or unsubstituted pyrrole (represented by Formula 8, which can be, e.g., the pyrrole of Formula 4 of Formula 6, prepared as described above).

The vilsmeier-Haack acylation is conducted as described above with reference to Reaction Scheme 1 and the preparation of the 2-(lower alkyl substituted)pyrrole starting material. A substituted or unsubstituted pyrrole of Formula 8 is reacted with a compound of the Formula 7 where Z is Q (such as m-nitrobenzoylmorpholine) under the conditions previously described to yield the 2-(3'-nitrobenzoyl)pyrrole intermediate of Formula 9.

Alternatively, about 0.5 to 2 molar equivalents of m-nitrobenzoyl chloride (Formula ;b 7 where Z is chloro) (available from Aldrich) is added to pyrrole or an optionally substituted pyrrole (represented by Formula 8, prepared, e.g., as described in Reaction Schemes 1 and 2) dissolved in an inert organic solvent (preferably toluene) and heated, preferably to the reflux temperature of the solvent used, in an inert atmosphere (e.g., under nitrogen). The reaction takes place over a period of about 1 to 30 hours, preferably 10 to 25 hours, and most preferably about 18 hours. The 2-(3'-nitrobenzoyl)pyrrole intermediate of Formula 9 is isolated and purified in the usual manner.

Preparation of Intermediate (10)

A compound of Formula 9 is dissolved in an inert organic solvent (such as methanol or a methanol: THF mixture) and subjected to catalytic hydrogenation (preferably using a 10% palladium-charcol catalyst) at elevated pressure (about 45 p.s.i.). The reaction takes place over a period of about 15 minutes to 6 hours, preferably 30 minutes to 4 hours, and most preferably about 1 hour. A temperature range of about −10° C. to 120° C., preferably −10° C. to 40° C., and most preferably ambient temperature is used. The 2-(3'-aminobenzoyl)pyrrole intermediate of Formula 10 is isolated and purified in the usual manner.

Preparation of Intermediate (11)

A compound of Formula 10 is dissolved in an inert organic solvent (preferably anhydrous tetrahydrofuran) and added slowly to a stirred suspension of a reducing agent (such as a hydride of aluminum or boron; preferably LAH) in the same or a similar solvent. The reaction mixture is heated, most preferably at the reflux temperature of the solvent used, for a period of about 5 minutes to 1 hour, preferably 10 minutes to 45 minutes, and most preferably about 30 minutes. The reaction mixture is then cooled (to about 0° C.) and the excess reducing agent is destroyed by carefully adding a combination of ethyl acetate, saturated sodium sulfate solution and solid anhydrous sodium sulfate. The insoluble material is removed by filtration and the filrate evaporated in vacuo to produce a 2-(3'-amino-α-hydroxybenzyl)pyrrole (not shown), an unstable intermediate that is used without further purification.

A 2-(3'-amino-α-hydroxybenzyl)pyrrole is dissolved in an inert organic solvent (such as a lower alkanol, preferably methanol), cooled to about −20° to 10° C., preferably −5° C., and treated with a molar excess of a reducing agent (such as sodium cyanoborohydride in glacial acetic acid). The reaction mixture is allowed to warm to about ambient temperature and is stirred for a period of about 0.5 to 36 hours, preferably 1 to 18 hours, and most preferably about 2 hours. The reaction is then quenched (e.g., with saturated sodium carbonate) and extracted with ethyl acetate. The extract is washed with water, dried and evaporated in vacuo, and then purified, e.g., by column chromatography over slica gel, to obtain the 2-(3'-aminobenzyl)pyrrole of Formula 11.

Preparation of Intermediate (12)

A compound of Formula 11 is suspended in an inert organic solvent (such as methylene chloride, methylene chloride and methanol; preferably benzene). About two molar equivalents of sodium cyanate are added slowly, followed by the addition of a solution of about two molar equivalents of trifluoroacetic acid in the same or a similar inert solvent, optionally in an inert atmosphere (e.g., under nitrogen). The reaction takes place over a period of about 15 minutes to 100 hours, preferably 1 to 75 hours, and most preferably about 1 hour, depending on the substituents on the pyrrole ring. A temperature range of about −10° C. to 120° C., preferably =10° C. to 40° C., and most preferably ambient temperature is used. The reaction is quenched, e.g., by the addition of sodium carbonate, and the product is isolated and purified by the usual means to yield the 2-(3'-ureidobenzyl)-pyrrole of Formula 12.

Preparation of Formula I

A compound of Formula 12 is dissolved in an aqueous acid (such as glacial acetic acid, or hydrochloric acid with methanol and/or water) and subjected to catalytic hydrogenation (preferably using 5% rodium on activated alumina as the catalyst) at elevated pressure (about 45 p.s.i.). The reaction takes place over a period of about 30 minutes to 5 hours, preferably 1 to 2 hours, and most preferably about 1.5 hours. A temperature range of about −10° C. to 120° C., preferably −10° C. to 40° C., and most preferably ambient temperature is used. The catalyst is then separated by filtration, and the filtrate evaporated in vacuo. The residue is dissolved, if necessary, in an inert organic solvent (such as methylene chloride or ethyl acetate) and an oxidizing agent (preferably concentrated ammonium hydroxide) is added thereto. The organic phase is dried and evaporated in vacuo, purifying the residue by usual means (such as column chromatography over silica gel) to produce a N-lower alkyl-2-(3'-ureidobenzyl)pyrrolidine of Formula I.

Alternatively, a compound of Formula 11 can be saturated as described above to give the corresponding 2-(3'-aminobenzyl)pyrrolidine, followed by conversion to the N-lower alkyl-2-(3'-ureidobenzyl)pyrrolidine as described above in "Preparation of Intermediate 12."

Preparation of the Salts of Formula I

Some of the compounds of Formula I may be converted to corresponding acid addition salts. The conversion is accomplished by treatment with a stoichiometric amount of an appropriate acid, such as hydrochloric acid, sulfuric acid, methanesulfonic acid, HBr, or the like. Typically, the free base is dissolved in a polar organic solvent such as ethanol or methanol, and the acid added in water, ethanol or methanol. The temperature is maintained at 0°–50° C. The resulting salt precipitates spontaneously or may be brought out of solution with a less polar solvent.

The acid addition salts of the compounds of Formula I may be decomposed to the corresponding free bases by treating with an excess of a suitable base, such as ammonia or sodium bicarbonate, typically in the presence of aqueous solvent, and at a temperature of between 0° and 50° C. The free base form is isolated by conventional means, such as extraction with an organic solvent.

Preferred Processes and Last Steps

The compounds of the present invention can be prepared by contacting a 1-(lower alkyl)-2-(3'-ureidobenzyl)-5-(optionally lower alkyl substituted)pyrrole with a hydrogen donor to yield the corresponding 1-(lower alkyl)-2-(3'-ureido-benzyl)-5-(optionally lower alkyl substituted)pyrrolidine.

The compounds of the present invention can be prepared by hydrogenating a 1-(lower alkyl)-2-(3'-ureidobenzyl)-5-(optionally lower alkyl substituted)pyrrole with rhodium on activated alumina catalyst to yield the corresponding 1-(lower alkyl)-2-(3'-ureido-benzyl)-5-(optionally lower alkyl substituted)pyrrolidine.

The compounds of the present invention can be prepared by contacting a 2-(3'-aminobenzyl)-5-(optionally lower alkyl substituted)pyrrolidine with sodium cyanate and trifluoroacetic acid to yield the corresponding N-lower alkyl-2-(3'-ureidobenzyl)-5-(optionally lower alkyl substituted)pyrrolidine.

Preferred Compounds

The compounds of Formula I where $R^1$ is lower alkyl of one to four carbon atoms, preferably two or three carbon atoms are preferred, particularly where $R^1$ is propyl.

Also preferred are the compounds of Formula I where $R^2$ is hydrogen or lower alkyl of one to three carbon atoms.

The compounds of Formula I where $R^1$ and/or $R^2$ are n-(lower alkyl) are preferred.

The salts of Formula I are also preferred, especially the hydrochloride salts.

Particularly preferred are the compounds where:
$R^1$ is propyl and $R^2$ is methyl,
$R^1$ is propyl and $R^2$ is propyl, and
$R^1$ is ethyl and $R^2$ is hydrogen.

Most preferred is the compound where $R^1$ is propyl and $R^2$ is hydrogen, i.e., N-propyl-2-(3'-ureidobenzyl)-pyrrolidine, particularly the hydrochloride salt thereof.

Utility, Testing and Administration

General Utility

The compounds of this invention significantly reduce intraocular pressure without adverse side effects. They do not cause systemic cardiovascular effects when administered topically.

Testing

The compounds of the present invention are tested for utility in lowering IOP by contralateral eye studies in the rabbit, in which a test compound is administered to one eye of a group of test animals, and a control is administered to the other eye, and pressure measurements are taken over a period of time, for example, as described in Example 12.

Administration

The present compounds can be administered in a wide variety of dosage forms, either alone or in combination with other pharmaceutically compatible medicaments in the form of pharmaceutical compositions suited for ophthalmic administration. The pharmaceutical carrier can be either a solid material or a liquid in which the compound is dissolved, dispersed or suspended, and can optionally contain small amounts of preservatives and/or pH buffering agents.

The liquid compositions can, for example, be in the form of solutions, emulsions, suspensions, creams, or ointments. The solid compositions can take the form of sustained release ocular insert devices and the like.

One aspect of this invention concerns a novel method for the treatment of certain ophthalmic diseases in mammals, particularly those diseases associated with or caused by increased intraocular pressure such as for example, glaucoma.

Ophthalmic preparations are sterile products for either topical application to the eyelids or instillation into the space (cul-de-sac) between the eyeball and the eyelids. Presently available ophthalmic preparations include solutions, suspensions, and ointments. Presently available topical treatment of eye diseases include topically applied ophthalmic drops, solutions, suspensions or ointment or their subconjunctival injection.

The composition of this invention comprises, as an active ingredient, a compound of this invention or a salt thereof in admixture with an ophthalmologically acceptable excipient.

An excipient is ophthalmologically acceptable if it is non-irritating. It is advantageous if it enables the active ingredient to penetrate the blood-aqueous barrier and/or to difuse to or through the various ocular substructures to the site where it is pharmacologically active.

The ophthalmic composition may be aqueous or non-aqueous, and it may be in the form of a solution, suspension, gel, ointment, slow release polymer, or other. Amount of active ingredient in the composition will vary with the particular formulation and disease state but generally will be between 0.01 to 1.0% wt/vol of active ingredient. An individual application dose, preferably about one drop (or about 50 μl), will contain about 0.5 μg to about 0.5 mg of active ingredient.

Pharmaceutical ophthalmic compositions are typically sterilized aqueous solutions (e.g., eyedrops) containing 0.01% to 1% wt/vol.; most preferably 0.025% to 0.5% of the active ingredient, along with suitable buffer system, solubilizer, and preservative. The total concentration of solutes should be such that, the resulting solution is isotonic with the lacrimal fluid by addition of a tonicifier, e.g., NaCl or manitol (through this is not absolutely necessary) and has an equivalent pH in the range of pH 6–8, preferably 7.4. Typically preservatives are phenylmercuric acetate, chlorobutanol, thimerosal, and benzalkonium chloride. Typical buffers and salts are based on, e.g., citrate, phosphate or borate; solubilizers include glycerin and polysorbate 80.

The aqueous solutions are formulated by dissolving a compound of the present invention in a solubilizer, adding water, a buffer, a tonicifier and a preservative, adjusting the pH to about 6.0–8.0, making a final volume adjustment with additional water, and sterilizing the preparation using methods known to those in the art.

EXAMPLES

The following preparations and examples are given to enable those skilled in the art to more clearly understand and to practice the present invention. They should not be considered as limiting the scope of the invention, but merely as being illustrative and representative thereof.

PREPARATION 1

1-Propyl-2-(3'-ureidobenzyl)-5-ethylpyrrole

1A. Formula 3 Where Q is Methyl-2-Acetylpyrrole 139 g (1.07 mol) of N-acetylmorpholine, cooled to 0° C. was treated dropwise, under stirring, with 15 g (1 mol) of phosphorus oxychloride. When the addition was completed the temperature was slowly raised to 30° C. and maintained at this temperature for 24 hours. The mixture was then cooled to 0° C. an a solution of 67 g (1 mol) of pyrrole in 500 ml of anhydrous 1,2-dichloroethane was added dropwise, stirring for 24 additional hours at room temperature. It was then slowly poured into 4000 ml of saturated sodium carbonate solution (bringing the pH to 12) and refluxed under stirring for 2 hours further. After cooling, the solid material was filtered through celite and washed with 20 liters of methylene chloride. The filtrate was separated into two phases, the organic phase was dried and evaporated under vacuo. The residue was purified by column chromatography on 2 Kg of silica gel, using methylene chloride as eluant, thus obtaining 41.2 g (35%) of 2-acetylpyrrole, the title compound.

1B. Formula 6 Where $R^1$ is Propyl and $R^2$ is Ethyl:1-Propyl-2-acetylpyrrole 10.6 g (440 mmol) of 60% sodium hydride were suspended under nitrogen atmosphere in 100 ml of anhydrous dimethylformamide. A solution of 20 g (183 mmol) of 2-acetylpyrrole in 100 ml of anhydrous dimethylformamide was added thereto, in a dropwise fashion and under stirring, maintaining the temperature at 23°–35° C. The resulting mixture was stirred for an additional hour and then treated dropwise with a solution of 23 ml (250 mmol) of 1-bromopropane in 50 ml of dry dimethylformamide. The reaction mixture was kept at room temperature for 20 hours, and thereafter poured into 1000 ml of ethyl acetate, washed with water (5×500 ml), dried and evaporated in vacuo. Purification of the residue by column chromatography on 500 g of silica gel, using hexane-ethyl acetate (95:5) as eluant provided 24 g (88%) of the title compound, 1-propyl-2-acetylpyrrole, as an oil.

1C. Formula 4 Where $R^1$ is Propyl and $R^2$ is Ethyl: 1-Propyl-2-ethylpyrrole To a stirred suspension of 4 g (130 mmol) of lithium aluminum hydride in 500 ml of anhydrous tetrahydrofuran was added dropwise, at room temperature, a solution of 23.5 g (155 mmol) of 1-propyl-2-acetylpyrrole in 100 ml of anhydrous tetrahydrofuran. The reaction mixture was refluxed for 1 hour, cooled to 0° C. and the excess reagent destroyed by carefully adding ethyl acetate, saturated sodium sulfate solution and solid anhydrous sodium sulfate. The insoluble material was separated by filtration and the filtrate in vacuo. The unstable 1-propyl-2α-hydroxyethylpyrrole thus obtained 23 g (150 mmol) was dissolved in 250 ml of methanol, the solution cooled to −10° C. and treated with 83 ml of glacial acetic acid and 18.8 g (290 mmol) of sodium cyanoborohydride. The reaction mixture was allowed to attain room temperature and stirred for an additional hour. It was then slowly poured into 600 ml of saturated sodium carbonate solution and the product extracted with ethyl acetate (3×500 ml). The combined extracts were washed with water (1×500 ml), dried and evaporated in vacuo. The residue was purified by column chromatography on 500 g of silica gel, usin hexane as the eluting solvent, thus obtaining 7.7 g (36%) of the title compound, 1-propyl-2-ethylpyrrole, as an oil.

1D. Formula 9 Where $R^1$ is Propyl and $R^2$ is Ethyl: 1-Propyl-2-(3′-nitrobenzoyl)-5-ethylpyrrole A solution of 7 g (51 mmol) of 1-propyl-2-ethylpyrrole in 100 ml of toluene was treated with 14 g (75 mmol) of m-nitrobenzoyl chloride. The reaction mixture was heated to reflux temperature, under nitrogen atmosphere, during 18 hours. It was then cooled and purified by column chromatography on 500 g of deactivated alumina using hexane-acetone (90:10) as eluant, to produce 13 g (89%) of the title compound, 1-propyl-2-(3′-nitrobenzoyl)-5-ethylpyrrole, which was recrystallized from methylene chloride-hexane. M.P. 43°–45° C.

1E. Formula 10 Where $R^1$ is Propyl and $R^2$ is Ethyl: 1-Propyl-2-(3′-aminobenzoyl)-5-ethylpyrrole A solution of 12 g (41 mmol) of 1-propyl-2-(3′-nitrobenzoyl)-5-ethylpyrrole in 200 ml of a (1:1) methanol-tetrahydrofuran mixture was hydrogenated at 45 p.s.i. in the presence of 2.4 g of 10% palladium-charcoal catalyst. After 1 hour the catalyst was separated by filtration and the filtrate evaporated in vacuo, thus obtaining 10 g (93%) of the title compound, 1-propyl-2-(3′-aminobenzoyl)-5-ethylpyrrole, which was recrystallized from methylene chloride-hexane.
M.P. 59°–61° C.

1F. Formula 11 Where $R^1$ is Propyl and $R^2$ is Ethyl: 1-Propyl-2-(3′-aminobenzyl)-5-ethylpyrrole To a stirred suspension of 2 g (50 mmol) of lithium aluminum hydride in 100 ml of anhydrous tetrahydrofuran was added dropwise, at room temperature, a solution of 12 g (46 mmol) of 1-propyl-2-(3′-aminobenzoyl)-5-ethylpyrrole in 100 ml of anhydrous tetrahydrofuran. The reaction mixture was refluxed for 15 minutes, cooled to 0° C. and the excess reagent destroyed by carefully adding ethyl acetate, saturated sodium sulfate solution and solid anhydrous sodium sulfate. The insoluble material was separated by filtration and the filtrate evaporated in vacuo, to produce 11.1 g (43 mmol) of 1-propyl-2-(3′-amino-α-hydroxybenzyl)-5-ethylpyrrole. This crude compound was dissolved in 150 ml of methanol, cooled to −10° C. and treated with 23.5 ml of glacial acetic acid and 5.1 g (80 mmol) of sodium cyanoborohydride. The reaction mixture was warmed to room temperature and stirred for 18 additional hours. It was then poured into 500 ml of saturated sodium carbonate solution and the product extracted with ethyl acetate (4×300 ml). The combined extracts were washed with water (3×300 ml), dried and evaporated in vacuo. The residue was purified by column chromatography on 500 g of silica gel, using hexane-acetone (97:3) as eluant, thus obtaining 4.8 g (47%) of the title compound, 1-propyl-2-(3′-aminobenzyl)-5-ethylpyrrole, as an oil.

1G. Formula 12 Where $R^1$ is Propyl and $R^2$ is Ethyl: 1-Propyl-2-(3′-ureidobenzyl)-5-ethylpyrrole A solution of 3.5 ml (39 mmol) of trifluoroacetic acid in 200 ml of methylene chloride was added dropwise, over a 2 hour period and under nitrogen atmosphere, to a stirred suspension of 4.8 g (19 mmol) of 1-propyl-2-(3′-aminobenzyl)-5-ethylpyrrole and 2.58 g (39 mmol) of sodium cyanate in 400 ml of anhydrous methylene chloride and 90 ml of methanol. The reaction mixture was stirred at room temperature for 18 additional hours, 2 g (18 mmol) of sodium carbonate were added and the solvent evaporated under reduced pressure. The residue was purified by column chromatography on 300 g of silica gel, using hexane-acetone (1:1) as eluant, obtaining 4.04 g (72%) of the title compound, 1-propyl-2-(3′-ureidobenzyl)-5-ethylpyrrole, which was recrystallized from ether-hexane. M.P. 116°–118° C.

1H. Formula 12 Where $R^1$ is Propyl and $R^2$ is Methyl: 1-Propyl-2-(3′-ureidobenzyl)-5-methylpyrrole By following the procedures of Preparations 1A through 1G above and substituting 1-formylmorpholine for 1-acetylmorpholine, there is obtained 1-propyl-2-(3′-ureidobenzyl)-5-methylpyrrole.

PREPARATION 2

1-Butyl-2-(3′-ureidobenzyl)-5-ethylpyrrole

2A. Formula 6 Where $R^1$ is Butyl and $R^2$ is Ethyl: 1-Butyl-2-acetylpyrrole 10.6 g (440 mmol) of 60% sodium hydride were suspended, under nitrogen atmosphere, in 100 ml of anhydrous dimethylformamide and then a solution of 20 g (183 mmol) of 2-acetylpyrrole, prepared, for example, as described in Preparation 1A, in 100 ml of anhydrous dimethylformamide was added thereto, in a dropwise fashion and under stirring, at room temperature. The resulting mixture was stirred for 2 hours further and then treated dropwise with a solution of 25 ml (230 mmol) of 1-bromobutane in 50 ml of dry dimethylformamide. The reaction mixture was kept at room temperature for 18 additional hours, and thereafter poured into 1000 ml of ethyl acetate, washed with water (5×500 ml), dried and evaporated in vacuo, thus obtaining 16.9 g (56%) of the title compound, 1-butyl-2-acetylpyrrole, as an oil.

2B. Formula 4 Where $R^1$ is Butyl and $R^2$ is Ethyl:1-Butyl-2-ethylpyrrole

To a stirred suspension of 4 g (130 mmol) of lithium aluminum hydride in 300 ml of anhydrous tetrahydrofuran was added dropwise, at room temperature, a solution of 27 g (160 mmol) of 1-butyl-2-acetylpyrrole in 200 ml of anhydrous tetrahydrofuran. The reaction mixture was refluxed for 30 minutes, cooled to 0° C. and the excess reagent destroyed by carefully adding ethyl acetate, saturated sodium sulfate solution and solid anhydrous sodium sulfate. The insoluble material was separated by filtration and the filtrate evaporated under reduced pressure, to produce 1-butyl-2-α-hydroxyethylpyrrole. This unstable crude alcohol 26 g (150 mmol) was dissolved in 250 ml of methanol, cooled to −10° C. and thereafter 101 ml of glacial acetic acid and 22.8 g (360 mmol) of sodium cyanoborohydride were added thereto. The reaction mixture was allowed to attain room temperature and stirred for 1 hour. It was then poured into 600 ml of saturated sodium carbonate solution and the product extracted with ethyl acetate (5×300 ml). The combined extracts were washed with water (2×300 ml), dried and evaporated in vacuo. Purification of the residue by column chromatography on 500 g of silica gel, using hexane-acetone (90:10) as eluant, provided 20 g (81%) of the title compound, 1-butyl-2-ethylpyrrole, as an oil.

2C. Formula 9 Where $R^1$ is Butyl and $R^2$ is Ethyl:1-Butyl-2-(3'-nitrobenzoyl)-5-ethylpyrrole A solution of 19 g (160 mmol) of 1-butyl-2-ethylpyrrole in 300 ml of toluene was treated with 38 g (200 mmol) of m-nitrobenzoyl chloride. The reaction mixture was refluxed under nitrogen atmosphere for 18 hours, cooled and purified by column chromatography on 1 Kg of deactivated alumina (containing 3% water), using hexane-acetone (90:10) as eluant. There were obtained 13.2 g (35%) of 1-butyl-2-(3'-nitrobenzoyl)-5-ethylpyrrole, the title compound, as an oil.

2D. Formula 10 Where $R^1$ is Butyl and $R^2$ is Ethyl:1-Butyl-2-(3-aminobenzoyl)-5-ethylpyrrole A solution of 11.9 g (39 mmol) of 1-butyl-2-(3'-nitrobenzoyl)-5-ethylpyrrole in 100 ml of methanol was hydrogenated at 45 p.s.i. in the presence of 3 g of 10% palladium-charcoal catalyst for 1 hour. The catalyst was then separated by filtration and the filtrate evaporated under reduced pressure. The residue was purified by column chromatography on 500 g of silica gel, using hexane-acetone (95:5) as eluant, to produce 6.5 g (60%) of 1-butyl-2-(3'-aminobenzoyl)-5-ethylpyrrole, the pure title compound, which was recrystallized from hexane. M.P. 71°–7° C.

2E. Formula 11 Where $R^1$ is Butyl and $R^2$ is Ethyl:1-Butyl-2-(3'-aminobenzyl)-5-ethylpyrrole A solution of 6.1 g (23 mmol) of 1-butyl-2-(3'-aminobenzoyl)-5-ethylpyrrole in 50 ml of anhydrous tetrahydrofuran was added dropwise, at room temperature, to a stirred suspension of 1 g (28 mmol) of lithium aluminum hydride in 100 ml of anhydrous tetrahydrofuran. The resulting mixture was refluxed for 15 minutes, cooled to 0° C. and the excess reagent sodium sulfate solution and solid anhydrous sodium sulfate. The insoluble material was separated by filtration and the filtrate evaporated in vacuo. The unstable crude alcohol thus obtained, 1-butyl-2-(3'-amino-α-hydroxybenzyl)-5-ethylpyrrole (6.1 g, 23 mmol) was dissolved in 75 ml of methanol, cooled to −10° C. and treated with 13 ml of glacial acetic acid and 2.8 g (44 mmol) of sodium cyanoborohydride. The reaction mixture was stirred at room temperature for 1 hour, poured into 200 ml of saturated sodium carbonate solution and the product extracted with ethyl acetate (4×300 ml). The combined extracts were washed with water (3×150 ml), dried and evaporated under reduced pressure. The residue was purified by column chromatography on 300 g of silica gel using hexane-acetone (95:5) as eluant, thus obtaining 3.5 mg (61%) of the title compound, 1-butyl-2-(3'-aminobenzyl)-5-ethylpyrrole, as an oil.

2F. Formula 12 Where $R^1$ is Butyl and $R^2$ is Ethyl:1-Butyl-2-(3'-ureidobenzyl)-5-ethylpyrrole A stirred solution of 3.1 g (12 mmol) of 1-butyl-2-(3'-aminobenzyl)-5-ethylpyrrole in 250 ml of dry methylene chloride and 50 ml of anhydrous methanol was treated, at room temperature and under nitrogen atmosphere, with 1.7 g (26 mmol) of sodium cyanate, followed by the dropwise addition, over a 2 hour period, of 2.3 ml (29 mmol) of trifluoroacetic acid in 100 ml of methylene chloride. The reaction mixture was stirred at room temperature for 18 additional hours, 2 g (18 mmol) of sodium carbonate were then added and the solvent evaporated under reduced pressure. The residue was purified by column chromatography on 300 g of silica gel, using methylene chloride-methanol (97:3) as eluant, thus obtaining 3.4 g (93%) of the title compound, 1-butyl-2-(3'-ureidobenzyl)-5-ethylpyrrole, which was recrystallized from ether-hexane. M.P. 103°–106° C.

PREPARATION 3

1-Methyl-2-(3'-ureidobenzyl)pyrrole

3A. Formula 9 Where $R^1$ is Hydrogen and $R^2$ is Hydrogen:2-(3'-Nitrobenzyl)pyrrole A solution of 50 g (270 mmol) of m-nitrobenzoyl chloride in 1500 ml of toluene was heated to reflux and treated dropwise, over a 3 hour period and under nitrogen atmosphere, with a solution of 50 g (750 mmol) of pyrrole in 1000 ml of toluene, refluxing the mixture for 20 hours further. It was then cooled and purified by column chromatography on 2.5 Kg of deactivated alumina. The fractions eluted with hexane-ethyl acetate (80:20) afforded 24 g (41%) of the title compound, 2-(3'-nitrobenzoyl)pyrrole, which was recrystallized from methylene chloride. M.P. 134°–136° C.

3B. Formula 6 Where $R^1$ is Methyl and $R^2$ is Hydrogen:1-Methyl-2-(3'-nitrobenzoyl)pyrrole 50% Sodium hydride 2.15 g (89 mmol) was suspended, under nitrogen atmosphere, in 100 ml of anhydrous dimethylformamide. A solution of 10 g (46 mmol) of 2-(3'-nitrobenzoyl)pyrrole in 50 ml of anhydrous dimethylformamide was added thereto, and the resulting mixture stirred for 1 hour, cooled to 0° C. and then treated dropwise with a solution of 8.6 ml (130 mmol) of methyl iodide in 30 ml of dry dimethylformamide. The reaction mixture was stirred for an additional hour at 0° C. and thereafter poured into 500 ml of ethyl acetate, the extract was washed with water (5×250 ml), dried and evaporated in vacuo. The residue was crystallized from methylene chloride-hexane, to produce 9.6 g (90%) of the title compound, 1-methyl-2-(3'-nitrobenzoyl)pyrrole. M.P. 115°–117° C. (methylene chloride-methanol)

3C. Formula 10 Where $R^1$ is Methyl and $R^2$ is Hydrogen: 1-Methyl-2-(3'-aminobenzoyl)pyrrole A solution of 9 g (39 mmol) of 1-methyl-2-(3'-nitrobenzoyl)pyrrole in 150 ml of a (2:1) methanol-tetrahydrofuran mixture was hydrogenated at 45 p.s.i. in the presence of 2 g of 10% palladium-charcoal catalyst, for 30 minutes. The catalyst was separated by filtration and the filtrate evaporated under vacuum. Crystallization of the residue from acetone-hexane provided 6.63 g (85%) of the title compound, 1-methyl-2-(3'-aminobenzoyl)pyrrole. M.P. 84°–86° C.

3D. Formula 11 Where $R^1$ is Methyl and $R^2$ is Hydrogen:1-Methyl-2-(3'-aminobenzyl)pyrrole To a stirred suspension of 2 g (50 mmol) of lithium aluminum hydride in 100 ml of anhydrous tetrahydrofuran was added dropwise, at room temperature and under nitrogen atmosphere, a solution of 9 g (45 mmol) of 1-methyl-2-(3'-aminobenzoyl)pyrrole in 100 ml of anhydrous tetrahydrofuran. The reaction mixture was refluxed for 15 minutes, cooled to 0° C. and the excess reagent destroyed by carefully adding ethyl acetate, saturated sodium sulfate solution and solid anhydrous sodium sulfate. The insoluble material was separated by filtration and the filtrate evaporated in vacuo. The unstable 1-methyl-2-(3'-amino-α-hydroxybenzyl)pyrrole thus obtained (9 g, 45 mmol) was dissolved in 150 ml of methanol, cooled to 0° C. and treated with 24 ml (419 mmol) of glacial acetic acid and 5.67 g (90 mmol) of sodium cyanoborohydride. The reaction mixture was stirred at room temperature for 18 hours, poured into 500 ml of saturated sodium carbonate solution and the product extracted with ethyl acetate (3×500 ml). The combined extracts were washed with water (3×300 ml), dried and evaporated in vacuo. The residue was purified by column chromatography on 600 g of silica gel, using hexane-ethyl acetate (80:20) as eluant, obtaining 4.89 g (67%) of the title compound, 1-methyl-2-(3'-aminobenzyl)pyrrole, which was recrystallized from acetone-hexane.
M.P. 77°–79° C.

3E. Formula 12 Where $R^1$ is Methyl and $R^2$ is Hydrogen:1-Methyl-2-(3'-ureidobenzyl)pyrrole To a stirred solution of 4.4 g (23 mmol) of 1-methyl-2-(3'-aminobenzyl)pyrrole in 400 ml of benzene there were added 3.08 g (47 mmol) of sodium cyanate followed by the dropwise addition of a solution of 3.65 ml (47 mmol) of trifluoroacetic acid in 300 ml of benzene. When the addition was completed, the reaction mixture was stirred at room temperature for 1 hour further and then poured into 500 ml of saturated sodium carbonate solution. The organic phase was separated and the aqueous layer extracted with ethyl acetate (3×500 ml). The combined extracts were washed with water (1×500 ml), dried and evaporated under reduced pressure. The residue was purified by column chromatography on 500 g of silica gel, using methylene chloride-acetone (80:20) as eluant, thus obtaining 5.1 g (90%) of the title compound, 1-methyl-2-(3'-ureidobenzyl)pyrrole, which was recrystallized from acetone-hexane.
M.P. 143°–145° C.

PREPARATION 4

1-Ethyl-2-(3'-ureidobenzyl)pyrrole

4A. Formula 6 Where $R^1$ is Ethyl and $R^2$ is Hydrogen:1-Ethyl-2-(3'-nitrobenzoyl)pyrrole 3.2 g (130 mmol) of 50% sodium hydride were suspended, under nitrogen atmosphere, in 100 ml of anhydrous dimethylformamide. A solution of 12 g (55 mmol) of 2-(3'-nitrobenzoyl)pyrrole, prepared, for example, as described in Preparation 3A, in 50 ml of dimethylformamide was added thereto, at room temperature and under stirring. The resulting mixture was stirred for an additional hour and then treated dropwise with a solution of 11.2 ml (70 mmol) of ethyl iodide in 30 ml of dry dimethylformamide. The reaction mixture was stirred for an additional hour and then poured into 500 ml of ethyl acetate. The organic extract was washed with water (5×250 ml), dried and evaporated in vacuo. Crystallization of the residue from acetone-hexane afforded 10.55 g (78%) of 1-ethyl-2-(3'-nitrobenzoyl)pyrrole, the title compound.
M.P. 56°–58° C. (methylene chloride-methanol)

4B. Formula 10 Where $R^1$ is Ethyl and $R^2$ is Hydrogen:1-Ethyl-2-(3'-aminobenzoyl)pyrrole A solution of 10 g (45 mmol) of 1-ethyl-2-(3'-nitrobenzoyl)pyrrole in 150 ml of a (2:1) methanol-tetrahydrofuran mixture was hydrogenated at 45 p.s.i. in the presence of 2 g of 10% palladium-charcoal catalyst, for 45 minutes. The catalyst was then separated by filtration and the filtrate evaporated under reduced pressure, thus obtaining 8 g (91%) of the title compound, 1-ethyl-2-(3'-aminobenzoyl)pyrrole, which was recrystallized from hexane.
M.P. 47°–49° C.

4C. Formula 11 Where $R^1$ is Ethyl and $R^2$ is Hydrogen:1-Ethyl-2-(3'-aminobenzyl)pyrrole To a stirred suspension of 1.5 g (39 mmol) of lithium aluminum hydride in 100 ml of anhydrous tetrahydrofuran was added dropwise, at room temperature, a solution of 7.5 g (35 mmol) of 1-ethyl-2-(3'-aminobenzoyl)pyrrole in 100 ml of anhydrous tetrahydrofuran. The reaction mixture was refluxed for 15 minutes, cooled to 0° C. and the excess reagent destroyed by carefully adding ethyl acetate, saturated sodium sulfate solution and solid anhydrous sodium sulfate. The insoluble material was separated by filtration and the filtrate evaporated in vacuo. The unstable crude alcohol thus obtained, 1-ethyl-2-(3'-amino-α-hydroxybenzyl)pyrrole (7.5 g, 35 mmol) was dissolved in 100 ml of methanol, cooled to 0° C. and treated with 20 ml of glacial acetic acid and 4.7 g (78 mmol) of sodium cyanoborohydride. The reaction mixture was stirred at room temperature for 3 hours, poured into 600 ml of saturated sodium carbonate solution and the product extracted with ethyl acetate (3×500 ml). The combined extracts were washed with water (3×250 ml), dried and evaporated in vacuo. The residue was purified by column chromatography on 500 g of silica gel, using hexane-ethyl acetate (80:20) as eluant, thus obtaining 5.9 g (84%) of 1-ethyl-2-(3'-aminobenzyl)pyrrole, the title compound, as an oil.

4D. Formula 12 Where $R^1$ is Ethyl and $R^2$ is Hydrogen: 1-Ethyl-2-(3'-ureidobenzyl)pyrrole 1-Ethyl-2-(3'-aminobenzyl)pyrrole 5.6 g (28 mmol) was dissolved in a mixture of 500 ml of methylene chloride and 100 ml methanol; 3.92 g (60 mmol) of sodium cyanate were added to the solution and thereafter, in a dropwise fashion and at room temperature, 4.6 ml (59 mmol) of trifluoroacetic acid in 100 ml of methylene chloride. When the addition was completed, the resulting mixture was stirred for 72 hours, 10 g (90 mmol) of sodium carbonate were added thereto, the mixture stirred for 15 minutes and the solvent evaporated under reduced pressure. The residue was purified by column chromatography on 300 g of silica gel, using methylene chloride-acetone (85:15) as eluant, to produce 4.44 g (65%) of the title compound, 1-ethyl-2-(3'-ureidobenzyl)pyrrole, which was recrystallized from acetone-hexane.
M.P. 142°–145° C.

PREPARATION 5

1-Propyl-2-(3'-ureidobenzyl)pyrrole

5A. Formula 6 Where $R^1$ is Propyl and $R^2$ is Hydrogen: 1-Propyl-2-(3'-nitrobenzoyl)pyrrole 50% Sodium hydride 4 g (160 mmol) in mineral oil was suspended, under nitrogen atmosphere, in 250 ml of anhydrous dimethylformamide. A solution of 15 g (69 mmol) of 2-(3-nitrobenzoyl)pyrrole, prepared, for example, as described in Preparation 3A, in 50 ml of anhydrous dimethylformamide was added thereto, at room temperature, in a dropwise fashion and under stirring. The resulting mixture was stirred for 12 additional hours and then a solution of 18 ml (197 mmol) of 1-bromopropane in 50 ml of dry dimethylformamide was added. The reaction mixture was stirred for 18 hours further and thereafter poured into 1000 ml of ethyl acetate, washed with water (5×500 ml), dried and evaporated in vacuo. Purification of the residue by column chromatography on 500 g of silica gel, using hexane-ethyl acetate (90:10) as eluant provided 17.61 g (98%) of 1-propyl-2-(3'-nitrobenzoyl)pyrrole, the title compound, as an oil.

5B. Formula 10 Where $R^1$ is Propyl and $R^2$ is Hydrogen: 1-Propyl-2-(3'-aminobenzoyl)pyrrole A solution of 17.2 g (62 mmol of 1-propyl-2-(3'-nitrobenzoyl)pyrrole in 250 ml of methanol was stirred, under hydrogen atmosphere at 45 p.s.i., in the presence of 3 g of a 10% palladium-charcoal catalyst. After 1 hour the catalyst was separated by filtration and the filtrate evaporated under reduced pressure, thus obtaining 15 g (98%) of the title compound, 1-propyl-2-(3'-aminobenzoyl)pyrrole, as an oil.

5C. Formula 11 Where $R^1$ is Propyl and $R^2$ is Hydrogen: 1-Propyl-2-(3'-aminobenzyl)pyrrole A solution of 15.6 g (68 mmol) of 1-propyl-2-(3'-aminobenzoyl)pyrrole in 200 ml of anhydrous THF was added dropwise, at room temperature, to a stirred suspension of 3 g (78 mmol) of lithium aluminum hydride in 300 ml of anhydrous tetrahydrofuran. The reaction mixture was refluxed for 30 minutes, cooled to 0° C. and the excess reagent destroyed by carefully adding ethyl acetate, saturated sodium sulfate solution and solid anhydrous sodium sulfate. The insoluble material was separated by filtration and the filtrate evaporated in vacuo. The unstable crude alcohol thus obtained, 1-propyl-2-(3'-amino-α-hydroxybenzyl)pyrrole, (16 g) was immediately dissolved in 250 ml of methanol, cooled to 0° C. and treated with 66 ml of glacial acetic acid and 10.1 g (160 mmol) of sodium cyanoborohydride. The reaction mixture was stirred at room temperature for 1 hour, poured into 1000 ml of saturated sodium carbonate solution and the product extracted with ethyl acetate (3×500 ml). The combined extracts were washed with water (2×500 ml), dried and evaporated in vacuo. The residue was purified by column chromatograhy on 500 g of Florisil, using hexane-ethyl acetate (95:5) as eluant, thus obtaining 10.3 g (60%) of the title compound, 1-propyl-2-(3'-aminobenzyl)pyrrole, as an oil.

5D. Formula 12 Where $R^1$ is Propyl and $R^2$ is Hydrogen: 1-Propyl-2-(3'-ureidobenzyl)pyrrole A stirred solution of 5.15 g (24 mmol) of 1-propyl-2-(3'-aminobenzyl)pyrrole in 250 ml of benzene was treated, at room temperature, with 2.95 g (45 mmol) of sodium cyanate followed by the dropwise addition of 3.6 ml (46 mmol) of trifluoroacetic acid in 25 ml of benzene, stirring the reaction mixture for 3½ hours. It was then poured into 500 ml of saturated sodium carbonate solution, the organic phase was separated and the aqueous layer extracted with ethyl acetate (3×500 ml). The combined extracts were washed with water (2×300 ml), dried and evaporated in vacuo. Purification of the residue by column chromatography on 300 g of Florisil, using hexane-ethyl acetate (40:60) as the eluting solvent afforded 4.02 g (65%) of the title compound, 1-propyl-2-(3'-ureidobenzyl)pyrrole, which was recrystallized from ether.
M.P. 105°–107° C.

5E. Formula 12 Where $R^1$ is i-Propyl and $R^2$ is Hydrogen: 1-(i-Propyl)-2-(3'-ureidobenzyl)pyrrole By following the procedures of Preparation 5A through 5D above and substituting 2-bromproane for 1-bromopropane in Preparation 5A, there is obtained 1-(i-propyl)-2-(3'-ureidobenzyl)pyrrole.

5F. Formula 12 Where $R^1$ is Hexyl and $R^2$ is Hydrogen: 1-Hexyl-2-(3'-ureidobenzyl)pyrrole By following the procedures of Preparations 5A through 5D above and substituting 1-brmohexane for 1-bromopropane in Preparation 5A, there is obtained 1-hexyl-2-(3'-ureidobenzyl)pyrrole.

PREPARATION 6

1-Butyl-2-(3'-ureidobenzyl)pyrrole

6A. Formula 6 Where $R^1$ is Butyl and $R^2$ is Hydrogen: 1-Butyl-2-(3'-nitrobenzoyl)pyrrole 4 G (160 mmol) of 50% sodium hydride were suspended, under nitrogen atmosphere, in 250 ml of anhydrous dimethylformamide. A solution of 15 g (69 mmol) of 2-(3-nitrobenzoyl)pyrrole, prepared, for example, as described in Preparation 3A, in 50 ml of anhydrous dimethylformamide was added thereto, in a dropwise fashion and under stirring, maintaining the temperature at 20°–25° C. The resulting mixture was stirred for 2 additional hours and then a solution of 18 ml (170 mmol) of 1-bromobutane in 50 ml of dry dimethylformamide was added. The reaction mixture was stirred at room temperature for 18 hours further and then poured into 2000 ml of ethyl acetate. The organic extract was washed with water (5×500 ml), dried and evaporated in vacuo. The residue was purified by column chromatography on 1 Kg of silica gel, using hexane-acetone (90:10) as eluant, thus obtaining 18 g (95%) of 1-butyl-2-(3'-nitrobenzoyl)pyrrole, the title compound, as an oil.

6B. Formula 10 Where $R^1$ is Butyl and $R^2$ is Hydrogen:1-Butyl-2-(3'-aminobenzoyl)pyrrole A solution of 19 g (80 mmol) of 1-butyl-2-(3'-nitrobenzoyl)pyrrole in 250 ml of methanol was hydrogenated at 45 p.s.i. in the presence of 3 g of a 10% palladium-charcoal catalyst. After 45 minutes the catalyst was separated by filtration and the filtrate evaporated under reduced pressure. Purification of the residue by column chromatography on 750 g of silica gel, using hexane-ethyl acetate (75:25) as eluant, afforded 16.6 g (95%) of 1-butyl-2-(3'-aminobenzoyl)pyrrole, the title compound, as an oil.

6C. Formula 11 Where $R^1$ is Butyl and $R^2$ is Hydrogen:1-Butyl-2-(3'-aminobenzoyl)pyrrole To a stirred suspension of 5 g (130 mmol) of lithium aluminum hydride in 500 ml of anhydrous tetrahydrofuran was added dropwise, at room temperature, a solution of 16 g (66 mmol) of 1-butyl-2-(3'-aminobenzoyl)-pyrrole in 100 ml of anhydrous tetrahydrofuran. The reaction mixture was refluxed for 30 minutes, cooled to 0° C. and the excess reagent destroyed by carefully adding ethyl acetate, saturated sodium sulfate solution and solid anhydrous sodium sulfate. The insoluble material was separated by filtration and the filtrate evaporated in vacuo. The unstable crude alcohol thus obtained, 1-butyl-2-(3'-amino-α-hydroxybenzyl)pyrrole (16 g, 66 mmol), was immediately dissolved in 250 ml of methanol, cooled to 0° C. and treated with 66 ml of glacial acetic acid and 10.1 g (160 mmol) of sodium cyanoborohydride. The reaction mixture was stirred at room temperature for 1½ hours, poured into 1000 ml of saturated sodium carbonate solution and the product extracted with ethyl acetate (3×500 ml). The combined extracts were washed with water (2×300 ml) dried and evaporated in vacuo. The residue was purified by column chromatography on 750 g of silica gel using hexane-ethyl acetate (80:20) as eluant, thus obtaining 7.6 g (50%) of the title compound, 1-butyl-2-(3'-aminobenzyl)pyrrole, as an oil.

6D. Formula 12 Where $R^1$ is Butyl and $R^2$ is Hydrogen:1-Butyl-2-(3'-ureidobenzyl)pyrrole A solution of 3.5 ml (45 mmol) of trifluoroacetic acid in 25 ml of benzene was added dropwise to a suspension of 5 g (21 mmol) of 1-butyl-2-(3'-aminobenzyl)pyrrole and 2.85 g (43 mmol) of sodium cyanate in 250 ml of benzene. The reaction mixture was stirred at room temperature for 1 hour further and then poured into 600 ml of saturated sodium carbonate solution. The organic phase was separated and the aqueous phase extracted with ethyl acetate (3×300 ml). The combined extracts were washed with water (2×250 ml), dried and evaporated under reduced pressure. The residue was purified by column chromatography on 300 g of silica gel, using hexane-ethyl acetate (30:70) as eluant, thus obtaining 3.82 g (65%) of the title compound, 1-butyl-2-(3'-ureidobenzyl)pyrrole, which was recrystallized from acetone-hexane.
M.P. 102°-103° C.

PREPARATION 7

1-Butyl-2-(3'-ureidobenzyl)-5-propylpyrrole

7A. Formula 1 Where $R^2$ is Ethyl and Q is Morpholino:N-Propionylmorpholine

To 100 g (1.35 mol) of distilled propionic acid there were slowly added, under anhydrous conditions and under stirring, 144 g (1.21 mol) of thionyl chloride. The mixture was stirred at room temperature for 18 hours and then distilled at atmospheric pressure (585 mm). The fraction distilled at 68°-70° C. consisted of propionic acid chloride (76.8 g, 62% yield); 70 g. of this compound (760 mmol) were diluted with 1500 ml of anhydrous methylene chloride and treated dropwise, under stirring, with 170 g (1.95 mol) of morpholine. The reaction mixture was filtered and the filtrate washed with 10% aqueous hydrochloric acid (2×500 ml), with saturated sodium carbonate solution (2×500 ml) and water (2×500 ml), dried over sodium sulfate and evaporated in vacuo. The residue was distilled at 80°-82° C./0.1 mm Hg, to afford 82.2 g (76%) of the title compound, N-propionylmorpholine, as an oil.

7B. Formula 3 Where $R^2$ is Ethyl: 2-Propionylpyrrole

Phosphorus oxychloride 90 ml (960 mmol) was added dropwise, under stirring, to 100 g (699 mmol) of N-propionylmorpholine, maintaining the temperature of the reaction mixture between 35°-40° C. When the addition was completed the mixture was stirred for 12 additional hours and then 100 ml (1.44 mol) of pyrrole dissolved in 90 ml of anhydrous 1,2 dichloroethane was added, stirring for 24 hours further at room temperature. The mixture was then slowly poured into 3000 ml of saturated aqueous sodium carbonate solution, 1000 ml of 1,2-dichloroethane was added thereto and the mixture refluxed for 1 hour under vigorous stirring. It was the cooled, and the insolble material separated by filtration through celite. The organic phase from the filtrate was separated, dried and evaporated under reduced pressure. The residue was purified by column chromatography on 2 Kg of silica gel, using hexane-acetone (95:5) as eluant, thus obtaining 24 g (30%) of the title compound, 2-propionylpyrrole, as an oil.

7C. Formula 6 Where $R^1$ is Butyl and $R^2$ is Ethyl:1-Butyl-2-propionylpyrrole A solution of 20 g (162 mmol) of 2-propionylpyrrole was added dropwise to a stirred suspension of 6 g (250 mmol) of 50% sodium hydride in 100 ml of anhydrous dimethylformamide, under nitrogen atmosphere. The resulting mixture was stirred at room temperature for 2 hours and then 34 ml (322 mmol) of 1-bromobutane were added, stirring for 17 additional hours. The reaction mixture was then poured into 2000 ml of ethyl acetate and the organic extract washed with water (5×500 ml), dried and evaporated in vacuo. Purification of the residue by column chromatography on 1 Kg of silica gel, using hexane-acetone (97.5:2.5) as eluant provided 18.2 g (62%) of the title compound, 1-butyl-2-propionylpyrrole, as an oil.

7D. Formula 4 Where $R^1$ is Butyl and $R^2$ is Propyl:1-Butyl-2-propylpyrrole

To a stirred suspension of 4 g (100 mmol) of lithium aluminum hydride in 300 ml of anhydrous tetrahydrofuran was added dropwise, at room temperature, a solution of 18 g (100 mmol) of 1-butyl-2-propionylpyrrole in 100 ml of anhydrous tetrahydrofuran. The reaction mixture was refluxed for 30 minutes, cooled to 0° C. and the excess reagent destroyed by carefully adding ethyl acetate, saturated sodium sulfate solution and solid anhydrous sodium sulfate. The insoluble material was separated by filtration and the filtrate evaporated in vacuo. The unstable 1-butyl-2-(α-hydroxypropyl)pyrrole thus obtained (20 g, 110 mmol) was dissolved in 250 ml of methanol, the solution cooled to 0° C. and treated with 60 ml of glacial acetic acid and 14 g (220 mmol) of sodium cyanoborohydride. The reaction mixture was stirred at 0° C. for 30 minutes and thereafter for 75 minutes further at room temperature. It was then poured into 1000 ml of saturated sodium carbonate solution and the product extracted with ethyl acetate (3×500 ml). The combined extracts were washed with water (3×250 ml), dried and evaporated under reduced pressure. The residue was purified by column chromatography on 500 g of silica gel, using hexane-methylene chloride (95:5) as eluant, thus obtaining 8.7 g (52%) of the title compound, 1-butyl-2-propylpyrrole, as an oil.

7E. Formula 9 Where $R^1$ is Butyl and $R^2$ is Propyl:1-Butyl-2-(3'-nitrobenzoyl)-5-propylpyrrole To a solution of 8.7 g (50 mmol) of 1-butyl-2-propylpyrrole in 250 ml of toluene there were added 15 g (70 mmol) of m-nitrobenzoyl chloride. The reaction mixture was refluxed under nitrogen atmoshere for 16 hours, cooled and poured into a column of 1 Kg of deactivated alumina (containing 3% water). The fractions eluted with hexane-acetone (90:10) afforded 15 g (90%) of the title compound, 1-butyl-2-(3'-nitrobenzoyl)-5-propylpyrrole, as an oil.

7F. Formula 10 Where $R^1$ is Butyl and $R^2$ is Propyl:1-Butyl-2-(3'-aminobenzoyl)-5-propylpyrrole A solution of 13.8 g (43 mmol) of 1-butyl-2-(3'-nitrobenzoyl)-5-propylpyrrole in 200 ml of methanol was hydrogenated at 45 p.s.i. in the presence of 4 g of a 10% palladium-charcoal catalyst, for 30 minutes. The catalyst was separated by filtration and the filtrate evaporated under reduced pressure. Purification of the residue by column chromatography on 500 g of silica gel, using hexane-acetone (90:10) as eluant gave 8 g (64%) of the title compound, 1-butyl-2-(3'-aminobenzoyl)-5-propylpyrrole, as an oil.

7G. Formula 11 Where $R^1$ is Butyl and $R^2$ is Propyl:1-Butyl-2-(3'-aminobenzyl)-5-propylpyrrole To a stirred solution of 3 g (78 mmol) of lithium aluminum hydride in 300 ml of anhydrous tetrahydrofuran was added dropwise, at room temperature, a solution of 32 g (110 mmol) of 1-butyl-2-(3-aminobenzoyl)-5-propylpyrrole in 200 ml of anhyrous tetrahydrofuran. The reaction mixture was refluxed for 30 minutes, cooled to 0° C. and the excess reagent destroyed by carefully adding ethyl acetate, saturated sodium sulfate solution and solid anhydrous sodium sulfate. The insoluble material was separated by filtration and the filtrate evaporated in vacuo. The unstable 1-butyl-2-(-amino-α-hydroxybenzyl)-5-propylpyrrole compound thus obtained (32.2 g, 113 mmol) was dissolved in 500 ml of methanol, cooled to 0° C. and treated with 20 ml of glacial acetic acid and 10.6 g (169 mmol) of sodium cyanoborohydride. The reaction mixtue was stirred at 0° C. for 30 minutes, and thereafter for 1½ hours at room temperature. It was then poured into 500 ml of saturated sodium carbonate solution and the product extracted with ethyl acetate (3×500 ml). The combined extracts were washed with water (2×300 ml), dried and evaporated under reduced pressure. The residue was purified by column chromatography on 500 g of silica gel, using hexane: acetone (97.5:2.5) as eluant, to produce 20 g (66%) of 1-butyl-2-(3'-aminobenzyl)-5-propylpyrrole, the title compound, as an oil.

7H. Formula 12 Where $R^1$ is Butyl and $R^2$ is Propyl:1-Butyl-2-(3'-ureidobenzyl)-5-propylpyrrole A solution of 11.4 ml (148 mmol) of trifluoroacetic acid in 100 ml of methylene chloride was added dropwise to a mixture of 20 g (74 mmol) of 1-butyl-2-(3'-aminobenzyl)-5-propylpyrrole dissolved in 80 ml of methylene chloride, 20 ml of methanol, and 9.6 g (148 mmol) of sodium cyanate, at room temperature and under stirring. The reaction mixture was stirred for an hour further, poured into 500 ml of saturated sodium carbonate solution and extracted with 200 ml of methylene chloride and 200 ml of ethyl acetate. The combined extracts were washed with water, dried and evaporated under reduced pressure. The residue was purified by column chromatography on 500 g of silica gel, using methylene chloride-methanol (95:5) as eluant, to produce 21 g (91%) of the title compound, 1-butyl-2-(3'-ureidobenzyl)-5-propylpyrrole, which was recrystallized from acetone-hexane.

M.P. 85°–89° C.

7I. Formula 12 Where $R^1$ is Butyl and $R^2$ is i-Butyl:1-Butyl-2-(3'-ureidobenzyl)-5-propylpyrrole Similarly, by following the procedures of Preparations 7A through 7H and substituting B 2-methylpropionic acid for propionic acid in Preparation 7A, there is obtained 1-butyl-2-(3'-ureidobenzyl)-5-(i-butyl)pyrrole.

7J. Formula 12 Where $R^1$ is i-Propyl and $R^2$ is i-Butyl:1-(i-Propyl)-2-(3'-ureidobenzyl)-5-propylpyrrole Similarly, by following the procedures of Preparation 7I and substituting 2-bromopropane for 1-bromopropane in Preparation 7C, there is obtained 1-(i-propyl)-2-(3'-ureidobenzyl)-5-(i-butyl)pyrrole.

PREPARATION 8

1,5-Dipropyl-2-(3'-ureidobenzyl)pyrrole

8A. Formula 4 Where $R^2$ is Propyl:2-Propylpyrrole

To a stirred suspension of 13 g (340 mmol) of lithium aluminum hydride in 400 ml of anhydrous tetrahydrofuran was added dropwise, at room temperature, a solution of 12.8 g (100 mmol) of 2-propionylpyrrole, prepared, for example, as described in Preparation 7B, in 100 ml of anhydrous tetrahydrofuran. The reaction mixture was refluxed for 24 hours, cooled to 0° C. and the excess reagent destroyed by carefully adding ethyl acetate, saturated sodium sulfate solution and solid anhydrous sodium sulfate. The insoluble material was separated by filtration and the filtrate evaporated in vacuo. The residue was purified by column chromatography on 500 g of silica gel, using hexane-acetone (95:5) as eluant, to produce 8.7 g (76%) of the title compound, 2-propylpyrrole, as an oil.

8B. Formula 9 Where $R^2$ is Propyl:2-(3'-Nitrobenzoyl)-5-propylpyrrole

To a solution of 20 g (180 mmol) of 2-propyl-pyrrole in 500 ml of toluene, 50 g (270 mmol) of m-nitrobenzoyl chloride were added. The reaction mixture was refluxed under nitrogen atmosphere for 1½ hours, cooled and evaporated in vacuo. The residue was purified by column chromatography on 1 Kg of deactivated alumina (containing 3% water), using hexane-ethyl acetate (75:25) as eluant, to afford 16 g (34%) of the title compound, 2-(3'-nitrobenzoyl)-5-propylpyrrole, which was recrystallized from methylene chloride-methanol. M.P. 135°–137° C.

8C. Formula 6 Where $R^1$ is Propyl and $R^2$ is Propyl:1,5-Dipropyl-2-(3'-nitrobenzoyl)pyrrole 2.5 g (100 mmol) of 50% sodium hydride were suspended, under nitrogen atmosphere, in 150 ml of anhydrous dimethylformamide. A solution of 11.5 g (44 mmol) of 2-(3'-nitrobenzoyl)-5-propylpyrrole in 50 ml of anhydrous dimethylformamide was added thereto, in a dropwise fashion and under stirring. The resulting mixture was stirred at room temperature for an additional hour and then 10 ml (110 mmol) of 1-bromopropane was added. The reaction mixture was stirred at room temperature for 48 hours, and thereafter poured into 500 ml of ice-ethyl acetate. The organic phase was separated. The aqueous phase was extracted with more ethyl acetate (2×500 ml), and the combined orgainc extracts were washed with water (5×300 ml), dried and evaporated in vacuo. Purification of the residue by column chromatography on 500 g of silica gel, using hexane-acetone (90:10) as eluant provided 13.9 g (98%) of the title compound, 1,5-dipropyl-2-(3'-nitrobenzoyl)-pyrrole, as an oil.

8D. Formula 10 Where $R^1$ is Propyl and $R^2$ is Propyl:1,5-Dipropyl-2-(3'-aminobenzoyl)pyrrole A solution of 12.7 g (40 mmol) of 1,5-dipropyl-2-(3'-nitrobenzoyl)pyrrole in 100 ml of methanol was hydrogenated in the presence of 2.4 g of 10% palladium-charcoal catalyst, at room temperature and 45 p.s.i. After 4 hours the catalyst was separated by filtration and the filtrate evaporated to dryness under reduced pressure, to produce 10.5 g (91%) of the title compound, 1,5-dipropyl-2-(3'-aminobenzoyl)pyrrole, which was recrystallized from methylene chdloride-methanol. M.P. 65°–66° C.

8E. Formula 11 Where $R^1$ is Propyl and $R^2$ is Propyl:1.5-Dipropyl-2-(3'-aminobenzyl)pyrrole To a stirred suspensoin of 4 g (100 mmol) of lithium aluminum hydride in 1000 ml of anhydrous tetrahydrofuran was added dropwise, at room temperature, a solution of 11.9 g (44 mmol) of 1,5-dipropyl-2-(3'-aminobenzoyl)pyrrole in 200 ml of anhydrous tetrahydrofuran. The reaction mixture was refluxed for 30 minutes, cooled to 0° C. and the excess reagent destroyed by carefully adding ethyl acetate, saturated soldium sulfate solution and solid anhydrous sodium sulfate. The insoluble material was separated by filtration and the filtrate evaporated in vacuo. The unstable amino-α-hydroxybenzyl compound thus obtained (12 g, 44 mmol) was dissolved in 240 ml of methanol, cooled to 0° C. and treated with 15 ml of glacial acetic acid and 3.78 g (60 mmol) of sodium cyanoborohydride. The reaction mixture was stirred at room temperature for 1 hour, poured into 600 ml of saturated sodium carbonate solution and the product extracted with ethyl acetate (3×500 ml). The combined extracts were washed with water (3×300 ml), dried and evaporated in vacuo. The residue was purified by column chromatography on 300 g of silica gel, using hexane-ethyl acetate (90:10) as eluant, thus obtaining 10.5 g (93%) of the title compound, 1,5-dipropyl-2-(3'-aminobenzyl)pyrrole, as an oil.

8F. Formula 12 Where $R^1$ is Propyl and $R^2$ is Propyl:1,5-Dipropyl-2-(3'-ureidobenzyl)pyrrole A stirred solution of 2 g (7.7 mmol) of 1,5-dipropyl-2-(3'-aminobenzyl)pyrrole in 200 ml of benzene was treated with 1 g (15.3 mmol) of sodium cyanate followed by the dropwise addition, over a 1½ hour period, of a solution of 1.5 ml (19 mmol) of trifluoroacetic acid in 100 ml of benzene. The reaction mixture was stirred at room temperature for 1 more hour, poured into 300 ml of saturated aqueous sodium carbonate solution and extracted with ethyl acetate (3×300 ml). The combined extracts were washed with water (2×300 ml), dried and evaporated in vacuo. The residue was purified by column chromatography on 100 g of silica gel, using hexane-ethyl acetate (55:45) as eluant, thus obtaining 1.85 g (83%) of the title compound, 1,5-dipropyl-2-(3'-ureidobenzyl)pyrrole, which was recrystallized from acetone-hexane. M.P. 123°–126° C.

EXAMPLE 1

1-Propyl-2-(3'-ureidobenzyl)-5-ethylpyrrolidine hydrochloride (cis & trans isomers)

1A. Formula I where $R^1$ is Propyl and $R^2$ is Ethyl

A solution of 3.49 g (12 mmol) of 1-propyl-2-(3'-ureidobenzyl)-5-ethylpyrrole, prepared, for example, as described in Preparation 1, in 75 ml of glacial acetic acid was hydrogenated in the presence of 2.8 g of 5% rodium on activated alumina as catalyst, at 45 p.s.i. After 75 minutes, the catalyst was separated by filtration and the filtrate evaporated in vacuo. The residue was dissolved in 100 ml of ethyl acetate and 10 ml of concentrated ammonium hydroxide was added thereto. The organic phase was dried and evaporated in vacuo. The residue was purified by column chromatography on 300 g of silica gel, using a (70:30) mixture of methylene chloride-[chloroform:methanol:ammonium hydroxide (60:10:1)] to produce 900 mg (26%) of the cis isomer (the less polar) and the impure trans isomer, which was further purified by t.l.c., using a (20:80) mixture of methylene chloride-[CHCl$_3$:MeOH:NH$_4$OH (60:10:1)] as the eluting solvent, thus obtaining 150 mg (5%) of the pure compound. Upon treatment with the individual isomers with 1.5 molar equivalents of the 2.87N solution of hydrochloric acid in methanol there were obtained the corresponding hydrochloride salts, which were recrystallized from methanol-ether.

1-Propyl-2-(3'-ureidobenzyl)-5-ethylpyrrolidine .HCl salt—cis isomer—M.P. 227°–229° C.

1-Propyl-2-(3'-ureidobenzyl)-5-ethylpyrrolidine .HCl salt—trans isomer—M.P. 193°–195° C.

1B. Formula I Where $R^1$ is Propyl and $R^2$ is Methyl

By following the procedure of Example 1A and substituting 1-propyl-2-(3'-ureidobenzyl)-5-methylpyrrole for 1-propyl-2-(3'-ureidobenzyl)-5-ethylpyrrole, there is obtained 1-propyl-2-(3'-ureidobenzyl)-5-methylpyrrolidine hydrochloride—M.P. 201°–203° C.

EXAMPLE 2

1-Butyl-2-(3'-ureidobenzyl)-5-ethylpyrrolidine hydrochloride (cis & trans isomers)

A solution of 3.3 g (11 mmol) of 1-butyl-2-(3-ureidobenzyl)-5-ethylpyrrole in 100 ml of glacial acetic acid was hydrogenated in the presence of 2.7 g of 5% rodium on activated alumina as catalyst, at 45 p.s.i. for 1½ hours. The catalyst was then separated by filtration and the filtrate evaporated in vacuo. The residue was suspended in 100 ml of methylene chloride and 20 ml of concentrated ammonium hydroxide was added. The organic phase was dried and evaporated under reduced pressure. The residue was purified by column chromatography on 300 g of silica gel, using a (80:20) mixture of methylene chloride-[chloroform:methanol:ammonium hydroxide (60:10:1)], thus obtaining 1.2 g (36% of the cis isomer (the less polar product) and 330 mg (10%) of the trans isomer. Upon treatment of the individual isomers with 1.5 molar equivalents of a 2.87N solution of hydrochloric acid in methanol there were obtained the corresponding hydrochloride salts, which were recrystallized from methanol-ether.

1-Butyl-2-(3'-ureidobenzyl)-5-ethylpyrrolidine .HCl salt—cis isomer—M.P. 227°–229° C.

1-Butyl-2-(3'-ureidobenzyl)-5-ethylpyrrolidine .HCl salt—trans isomer—M.P. 193°–195° C.

EXAMPLE 3

1-Methyl-2-(3'-ureidobenzyl)pyrrolidine

A solution of 2 g (8.7 mmol) of 1-methyl-2-(3-ureidobenzyl)pyrrole, prepared, for example, as described in Preparation 3E, in 80 ml of glacial acetic acid was hydrogenated at 45 p.s.i. in the presence of 1.5 g of 5% rodium on activated alumina as catalyst, for 1 hour. The catalyst was then separated by filtration and the filtrate evaporated in vacuo. The residue was suspended in 100 ml of methylene chloride and 20 ml of ammonium hydroxide was added. The mixture was dried over sodium sulfate and evaporated under reduced pressure. Crystallization of the residue from acetone-ether afforded 870 mg (43%) of the title compound, 1-methyl-2-(3'-ureidobenzyl)pyrrolidine. M.P. 133°–135° C. (ether)

EXAMPLE 4

1-Ethyl-2-(3'-ureidobenzyl)pyrrolidine

A solution of 4 g (20 mmol) of 1-ethyl-2-(3'-ureidobenzyl)pyrrole, prepared, for example, as described in Preparation 4D, in 100 ml of glacial acetic acid was hydrogenated at 45 p.s.i. in the presence of 3 g of 5% rodium on activated alumina as catalyst, for 75 minutes. The catalyst was then separated by filtration and the filtrate evaporated in vacuo. The residue was suspended in 100 ml of methylene chloride and 20 ml of concentrated ammonium hydroxide was added. The mixture was dried over sodium sulfate and evaporated under reduced pressure. The residue was crystallized from ethyl acetate-hexane, to yield 2.26 g (46%) of the title compound, 1-ethyl-2-(3'-ureidobenzyl)pyrrolidine. M.P. 114°–116°

EXAMPLE 5

1-Propyl-2-(3'-ureidobenzyl)pyrrolidine

5A. Formula I Where $R^1$ is Propyl and $R^2$ is Hydrogen

1-Propyl-2-(3'-ureidobenzyl)pyrrole 2 g (7.7 mmol), prepared, for example, as described in Preparation 5D, was suspended in 80 ml of water and 20 ml of a 1.044M solution of hydrochloric acid (20 mmol) in methanol. This suspension was hydrogenated at 45 p.s.i. in the presence of 1.45 g of 5% rodium on activated alumina as catalyst, for 1 hour. The catalyst was then separated by filtration and the filtrate evaporated in vacuo. The aqueous residue was treated with ammonium hydroxide until an alkaline pH was obtained, and the product extracted with ethyl acetate (3×100 ml). The combined extracts were washed with water (2×50 ml), dried over sodium sulfate and evaporated under reduced pressure. The residue was crystallized from ethanol-water, thus obtaining 1.1 g (54%) of 1-propyl-2-(3'-ureidobenzyl)pyrrolidine, the title compound. M.P. 101°–104° C.

5B. Formula I Where $R^1$ is i-Propyl and $R^2$ is Hydrogen

By following the procedure of Example 5A and substituting 1-(i-propyl)-2-(3'-ureidobenzyl)pyrrole for 1-propyl-2-(3'-ureidobenzyl)pyrrole, there is obtained 1-(i-propyl)-2-(3'-ureidobenzyl)-5-methylpyrrolidine.

5C. Formula I Where $R^1$ is Hexyl and $R^2$ is Hydrogen

By following the procedure of Example 5A and substituting 1-hexyl-2-(3'-ureidobenzyl)pyrrole for 1-propyl-2-(3'-ureidobenzyl)pyrrole, there is obtained 1-hexyl-2-(3'-ureidobenzyl)-5-methylpyrrolidine.

EXAMPLE 6

1-Butyl-2-(3'-ureidobenzyl)pyrrolidine

A suspension of 1.25 g (4.6 mmol) of 1-butyl-2-(3'-ureidobenzyl)pyrrole, prepared, for example, as described in Preparation 6D, in a mixture of 75 ml of water, 75 ml of methanol and 10 ml of a 1N solution of hydrochloric acid in methanol, was hydrogenated at 45 p.s.i. in the presence of 1 g of 5% rodium on activated alumina as catalyst, for 1 hour. The catalyst was then separated by filtration and the filtrate evaporated in vacuo. The aqueous residue was treated with concentrated ammonium hydroxide until an alkaline pH was obtained, and the product extracted with ethyl acetate (3×50 ml). The combined extracts were washed with water (2×50 ml), dried and evaporated under reduced pressure. The residue was purified by column chromatography on 100 g of silica gel, using an (80:20) mixture of methylene chloride-[chloroform-methanol-ammonium hydroxide (60:10:1)] as the eluting system, thus obtaining 550 mg (44%) of the title compound, 1-butyl-2-(3'-ureidobenzyl)pyrrolidine, which was recrystallized from acetone-hexane. M.P. 80°–83° C.

EXAMPLE 7

1-Butyl-2-(3'-ureidobenzyl)-5-propylpyrrolidine (cis & trans isomers)

1A. Formula I Where $R^1$ is Butyl and $R^2$ is Propyl

A solution of 3 g (90 mmol) of 1-butyl-2-(3'-ureidobenzyl)-5-propylpyrrole in 150 ml of glacial acetic acid was hydrogenated at 45 p.s.i. in the presence of 2 g of 5% rodium on activated alumina as catalyst, for 4½ hours. The catalyst was then separated by filtration and the filtrate evaporated in vacuo. The residue was suspended in 100 ml of ethyl acetate, cooled to 0° C. and 30 ml of concentrated ammonium hydroxide was added thereto. The organic phase was separated, dried and evaporated in vacuo. The residue was purified by t.l.c. using a (50:50) mixture of chloroform-[chloroform:methanol:ammonium hydroxide (60:10:1)] as the eluant, to produce 1.1 g (37%) of the less polar cis-1-butyl-2-(3'-ureidobenzyl)-5-propylpyrrolidine isomer, and 150 mg (5%) of the more polar trans-1-butyl-2-(3'-ureidobenzyl)-5-propylpyrrolidine isomer, which was recrystallized from ether hexane.

The cis isomer was converted into the hydrochloride salt by reaction with 1.5 molar equivalents of a 2.87N solution of hydrochloric acid in methanol.

1-butyl-2-(3'-ureidobenzyl)-5-propylpyrrolidine .HCl salt—cis isomer—M.P. 238°-240° C. (acetone)

1-butyl-2-(3'-ureidobenzyl)-5-propylpyrrolidine— trans isomer—M.P. 138°-140° C. (ether-hexane)

7B. Formula I Where $R^1$ is Butyl and $R^2$ is i-Butyl

By following the procedure of Example 7A and substituting 1-butyl-2-(3'-ureidobenzyl)-5-(i-butyl)pyrrole for 1-butyl-2-(3'-ureidobenzyl)-5-propylpyrrole, there is obtained 1-butyl-2-(3'-ureidobenzyl)-5-(i-butyl)pyrrolidine.

7C. Formula I Where $R^1$ is i-Propyl and $R^2$ is i-Butyl

By following the procedure of Example 7A and substituting 1-(i-propyl)-2-(3'-ureidobenzyl)-5-(i-butyl)pyrrole for 1-butyl-2-(3'-ureidobenzyl)-5-propylpyrrole, there is obtained 1-(i-propyl)-2-(3'-ureidobenzyl)-5-(i-butyl)pyrrolidine.

EXAMPLE 8

1,5-Dipropyl-2-(3'-ureidobenzyl)pyrrolidine (cis & trans isomers)

A solution of 4.6 g (15 mmol) of 1,5-dipropyl-2-(3'-ureidobenzyl)pyrrole in 150 ml of glacial acetic acid was hydrogenated at 45 p.s.i. in the presence of 3.5 g of 5% rodium on activated alumina as catalyst, during 2 hours. The catalyst was then separated by filtration and the filtrate evaporated in vacuo. The residue was suspended in 100 ml of methylene chloride and 20 ml of ammonium hydroxide were added (to adjust pH to alkaline). Anhydrous sodium sulfate was added and the solvent evaporated under reduced pressure. The residue was purified by t.l.c. using an (80:20) mixture of chloroform [chloroform-methanol-ammonium hydroxide (60:10:1)] as the eluant, thus obtaining 1.83 g (39%) of the less polar cis-1,5-dipropyl-2-(3'-ureidobenzyl)pyrrolidine isomer (as an oil), and 214 mg (5%) of the more polar trans-1,5-dipropyl-2-(3'-ureidobenzyl)pyrrolidine isomer, which was recrystallized from ether-hexane.

1,5-dipropyl-2-(3'-ureidobenzyl)pyrrolidine—trans isomer—M.P. 140°-142° C.

The cis isomer was treated with 1.5 molar equivalents of a 2.87N solution of hydrochloric acid in methanol, to yield the hydrochloric salt, also an oil.

EXAMPLE 9

Ophthalmic Formulations

The following illustrates preparation of representative pharmaceutical formulations for ophthalmic solutions containing an active compound of Formula I, e.g., 1-propyl-2-(3'-ureidobenzyl)pyrrolidine.

| Ingredient | Amount |
| --- | --- |
| Active compound | 0.01 to 1.0% wt/vol. |
| Solubilizer | 0.1 to 2.0% wt/vol. |
| Purified Water | q.s. to dissolve above ingredients |
| Tonicifier | 0 to 1.5% wt/vol. |
| Buffer | 0.005 to 0.1% wt/vol. |
| Preservative | 0.0005 to 1.5% wt/vol. |
| Adjust the pH by addition of: | |
| Acid or Base | q.s. to adjust pH to 6.0-8.0 |
| Purified Water | q.s. to 100% |

Other compounds of Formula I, such as those prepared in accordance with Examples 1-8, can be used as the active compound in the preparation of opthalmic formulations per this Example.

EXAMPLE 10

Ophthalmic Formulations

The following illustrates representative pharmaceutical formulations for ophthalmic solutions containing an active compound of Formula I, e.g., 1-propyl-2-(3'-ureidobenzyl)pyrrolidine.

| Ingredient | Amount |
| --- | --- |
| Active compound | 0.01 to 1.0 to % wt/vol. |
| Polysorbate 80 | 0.1 to 2.0% wt/vol. |
| NaCl | 0.05 to 1.5% wt/vol. |
| Glacial Acetic Acid | 0.005 to 0.1% wt/vol. |
| Thimerosal | 0.0005 to 0.01% wt/vol. |
| Purified Water | q.s. to dissolve ingredients |
| NaOH or HCl | q.s. to adjust pH to 6.0-8.0 |
| Purified Water | q.s. to 100% |

Other compounds of Formula I, such as those prepared in accordance with Examples 1-8, can be used as the active compound in the preparation of ophthalmic formulations per this Example.

EXAMPLE 11

Ophthalmic Formulation

The following illustrates a preferred pharmaceutical formulation for an ophthalmic solution containing an active compound of Formula I, preferably, 1-propyl-2-(3'-ureidobenzyl)pyrrolidine.

| Ingredient | Amount |
| --- | --- |
| Active Compound | 0.5% wt/vol |
| Polysorbate 80 | 1.0% wt/vol |
| NaCl | q.s. to render isotonic |
| Glacial Acetic Acid | 0.03% wt/vol |
| Thimerosal | 0.004% wt/vol |
| Purified Water | q.s. to dissolve ingredients |
| NaOH or HCl | adjust pH to 7.4 |
| Purified Water | q.s. to 100% |

Other compounds of Formula I, such as those prepared in accordance with Examples 1-8, can be used as the active compound in the preparation of ophthalmic formulatons per this Example.

EXAMPLE 12

Reduction of Intraocular Pressure in Rabbits

This example illustrates the effect of compounds of the current invention on intraocular pressure (IOP).

Experimental Procedure

The effects of tested drug on intraocular pressure of the rabbit (using normal albino white New Zealand rabbits) is determined using a Digilab Model 30D pneuma-tonometer. Initial IOP readings are obtained in all animals after the administration of 50 μl of 0.5% Opthaine (proparacaine hydrochloride). A group of 4 rabbits serve as controls and are treated with 50 μl of saline in both eyes. Eight additional rabbits receive 50 μl of test drug (e.g., in a formulation such as distilled water adjusted to pH 7.4 with dilute acid, or prepared as described in one of the foregoing examples) in the right eye, and 50 μl of drug vehicle (the formulation without the active ingredient) in the contralateral left eye. IOP readings are made 30 minutes, 1 hour, 2 hours, and 4 hours after drug administration. Rabbits are observed for any signs of ocular irritation.

This procedure permits the comparison of drug treated eye with the contralateral vehicle treated eye, and also with saline treated eyes. for purposes of statistical analysis comparisons are made between the drug treated IOP values and vehicle treated contralateral eyes and also the saline treated IOP values.

Results

Compounds of the present invention demonstrate IOP lowering activity when tested by the above procedure. For example, results summarized in Table I show that the administration of a 0.5% solution of 1-propyl-2-(3'-ureidobenzyl)pyrrolidine, a test compound of the present invention, significantly decreased intraocular pressure in the right (treated) eyes of the experimental group.

TABLE 1

| Rabbit | Pressure (mm Hg) at Time | | | | |
|---|---|---|---|---|---|
| | 0 hr. | 30 min. | 1 hr. | 2 hr. | 4 hr. |
| Control | 20.1 ± 0.1 | 20.2 ± 0.4 | 21.2 ± 0.4 | 21.2 ± 0.5 | 21.1 ± 0.6 |
| Vehicle | 20.6 ± 0.8 | 22.0 ± 1.0 | 20.9 ± 1.1 | 20.8 ± 1.2 | 21.9 ± 1.1 |
| Test Eye | 20.1 ± 0.7 | 17.1 ± 1.1 | 18.1 ± 0.5 | 18.5 ± 1.0 | 21.1 ± 1.0 |

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A compound represented by the formula:

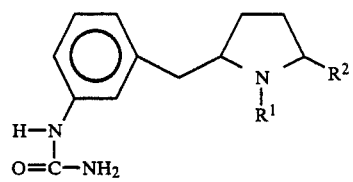

wherein:
  $R^1$ is lower alkyl; and
  $R^2$ is lower alkyl or hydrogen; or a pharmaceutically acceptable salt thereof; or any single isomer or mixture of isomers thereof.

2. The compound of claim 1 where $R^1$ is lower alkyl of one to four carbon atoms.

3. The compound of claim 2 where $R^2$ is hydrogen or lower alkyl of one to three carbon atoms.

4. The compound of claim 3 where lower alkyl is straight chain lower alkyl.

5. The compound of claim 4 where $R^1$ is methyl and $R^2$ is hydrogen.

6. The compound of claim 4 where $R^1$ is ethyl and $R^2$ is hydrogen.

7. The compound of claim 4 where $R^1$ is propyl.

8. The compound of claim 7 where $R^2$ is hydrogen.

9. The compound of claim 7 where $R^2$ is methyl.

10. The compound of claim 7 where $R^2$ is ethyl.

11. The compound of claim 7 where $R^2$ is propyl.

12. The compound of claim 4 where $R^1$ is butyl.

13. The compound of claim 12 where $R^2$ is hydrogen.

14. The compound of claim 12 where $R^2$ is methyl.

15. The compound of claim 12 where $R^2$ is ethyl.

16. The compound of claim 12 where $R^2$ is propyl.

17. A pharmaceutical composition for ophthalmic administration comprising an ophthalmologically acceptable non-toxic excipient and a therapeutically effective amount of a compound of claim 1.

18. A method of treating glaucoma in mammals, which comprises administering to a mammal suffering therewith a therapeutically effective amount of the compound of claim 1.

19. A method of treating glaucoma in mammals, which comprises administering to a mammal suffering therewith a therapeutically effective amount of the compound of claim 6.

20. A method of treating glaucoma in mammals, which comprises administering to a mammal suffering therewith a therapeutically effective amount of the compound of claim 8.

21. A method of treating glaucoma in mammals, which comprises administering to a mammal suffering therewith a therapeutically effective amount of the compound of claim 9.

22. A method of treating glaucoma in mammals, which comprises administering to a mammal suffering therewith a thereapeutically effective amount of the compound of claim 11.

* * * * *